US012714431B2

(12) United States Patent
Tillman et al.

(10) Patent No.: US 12,714,431 B2
(45) Date of Patent: Aug. 25, 2026

(54) MEDICAL IMPLANT AND METHODS OF MANUFACTURING THE MEDICAL IMPLANT

(71) Applicant: BOSTON SCIENTIFIC SCIMED, INC., Maple Grove, MN (US)

(72) Inventors: Josh Tillman, New Brighton, MN (US); Joshua Mark Inouye, Brooklyn Park, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 413 days.

(21) Appl. No.: 18/207,455

(22) Filed: Jun. 8, 2023

(65) Prior Publication Data

US 2023/0397912 A1 Dec. 14, 2023

Related U.S. Application Data

(60) Provisional application No. 63/350,520, filed on Jun. 9, 2022.

(51) Int. Cl.

*A61B 17/12* (2006.01)
*A61B 17/00* (2006.01)

(52) U.S. Cl.

CPC .. *A61B 17/12122* (2013.01); *A61B 17/12172* (2013.01); *A61B 2017/00632* (2013.01); *A61B 17/12177* (2013.01)

(58) Field of Classification Search

CPC ...... A61F 2/86; A61F 2/90; A61F 2/91; A61F 2/2418; A61F 2/2487; B21D 11/10;

(Continued)

(56) References Cited

U.S. PATENT DOCUMENTS

| | | | |
|---|---|---|---|
| 178,283 | A | 6/1876 | French |
| 1,967,318 | A | 7/1934 | Monahan |

(Continued)

FOREIGN PATENT DOCUMENTS

| | | | |
|---|---|---|---|
| CN | 1399571 | A | 2/2003 |
| CN | 202143640 | U | 2/2012 |

(Continued)

OTHER PUBLICATIONS

International Search Report and Written Opinion dated Aug. 3, 2004 for International Application No. PCT/US2004/008109.

(Continued)

*Primary Examiner* — Sarang Afzali
*Assistant Examiner* — Darrell C Ford
(74) *Attorney, Agent, or Firm* — Seager, Tufte & Wickhem LLP

(57) ABSTRACT

A method of manufacturing a medical implant for occluding a left atrial appendage may include cutting an expandable scaffold in a first configuration, wherein the expandable scaffold includes a plurality of struts having ends joined together at intersection points and a plurality of anchor members extending from the plurality of struts such that each anchor member extends from a medial portion of a strut of the plurality of struts, forming the expandable scaffold into a second configuration, wherein forming the expandable scaffold into the second configuration includes bending each anchor member along its bending axis, the bending axis being oriented parallel to a longitudinal axis of its respective strut of the plurality of struts, and heat setting the expandable scaffold in the second configuration. The method may include securing an occlusive element to the expandable scaffold.

14 Claims, 15 Drawing Sheets

(58) Field of Classification Search
CPC . B21D 22/02; B21F 45/008; Y10T 29/49805; Y10T 29/49863; Y10T 29/89865; Y10T 29/49908
USPC .................. 72/135; 29/421.1, 446, 447, 505
See application file for complete search history.

(56) References Cited

U.S. PATENT DOCUMENTS

| | | | |
|---|---|---|---|
| 3,402,710 | A | 9/1968 | Paleschuck |
| 3,540,431 | A | 11/1970 | Mobin-Uddin |
| 3,557,794 | A | 1/1971 | Van Patten |
| 3,638,652 | A | 2/1972 | Kelley |
| 3,811,449 | A | 5/1974 | Gravlee et al. |
| 3,844,302 | A | 10/1974 | Klein |
| 3,874,388 | A | 4/1975 | King et al. |
| 4,007,743 | A | 2/1977 | Blake |
| 4,108,420 | A | 8/1978 | West et al. |
| 4,175,545 | A | 11/1979 | Termanini |
| 4,309,776 | A | 1/1982 | Berguer |
| 4,341,218 | A | 7/1982 | Ü |
| 4,364,392 | A | 12/1982 | Strother et al. |
| 4,425,908 | A | 1/1984 | Simon |
| 4,545,367 | A | 10/1985 | Tucci |
| 4,585,000 | A | 4/1986 | Hershenson |
| 4,603,693 | A | 8/1986 | Conta et al. |
| 4,611,594 | A | 9/1986 | Grayhack et al. |
| 4,619,246 | A | 10/1986 | Molgaard-Nielsen et al. |
| 4,638,803 | A | 1/1987 | Rand et al. |
| 4,665,906 | A | 5/1987 | Jervis |
| 4,681,588 | A | 7/1987 | Ketharanathan et al. |
| 4,710,192 | A | 12/1987 | Liotta et al. |
| 4,718,417 | A | 1/1988 | Kittrell et al. |
| 4,759,348 | A | 7/1988 | Cawood et al. |
| 4,781,177 | A | 11/1988 | Lebigot |
| 4,793,348 | A | 12/1988 | Palmaz |
| 4,827,907 | A | 5/1989 | Tashiro |
| 4,832,055 | A | 5/1989 | Palestrant |
| 4,873,978 | A | 10/1989 | Ginsburg |
| 4,917,089 | A | 4/1990 | Sideris |
| 4,921,484 | A | 5/1990 | Hillstead |
| 4,960,412 | A | 10/1990 | Fink |
| 4,966,150 | A | 10/1990 | Etienne et al. |
| 4,998,972 | A | 3/1991 | Chin et al. |
| 5,037,810 | A | 8/1991 | Saliba, Jr. |
| 5,041,090 | A | 8/1991 | Scheglov et al. |
| 5,041,093 | A | 8/1991 | Chu |
| 5,042,707 | A | 8/1991 | Taheri |
| 5,053,009 | A | 10/1991 | Herzberg |
| 5,064,435 | A | 11/1991 | Porter |
| 5,071,407 | A | 12/1991 | Termin et al. |
| 5,078,736 | A | 1/1992 | Behl |
| 5,098,440 | A | 3/1992 | Hillstead |
| 5,108,418 | A | 4/1992 | Lefebvre |
| 5,108,420 | A | 4/1992 | Marks |
| 5,108,474 | A | 4/1992 | Riedy et al. |
| 5,116,360 | A | 5/1992 | Pinchuk et al. |
| 5,122,136 | A | 6/1992 | Guglielmi et al. |
| 5,133,733 | A | 7/1992 | Rasmussen et al. |
| 5,171,259 | A | 12/1992 | Inoue |
| 5,171,383 | A | 12/1992 | Sagaye et al. |
| 5,176,692 | A | 1/1993 | Wilk et al. |
| 5,192,301 | A | 3/1993 | Kamiya et al. |
| 5,211,658 | A | 5/1993 | Clouse |
| 5,234,458 | A | 8/1993 | Metais |
| 5,242,462 | A | 9/1993 | El-Nounnou et al. |
| 5,256,146 | A | 10/1993 | Ensminger et al. |
| 5,258,000 | A | 11/1993 | Gianturco |
| 5,258,042 | A | 11/1993 | Mehta |
| 5,279,539 | A | 1/1994 | Bohan et al. |
| 5,284,488 | A | 2/1994 | Sideris |
| 5,304,184 | A | 4/1994 | Hathaway et al. |
| 5,306,234 | A | 4/1994 | Johnson |
| 5,312,341 | A | 5/1994 | Turi |
| 5,329,942 | A | 7/1994 | Gunther et al. |
| 5,334,217 | A | 8/1994 | Das |
| 5,344,439 | A | 9/1994 | Otten |
| 5,350,398 | A | 9/1994 | Pavcnik et al. |
| 5,350,399 | A | 9/1994 | Erlebacher et al. |
| 5,353,784 | A | 10/1994 | Nady-Mohamed |
| 5,366,460 | A | 11/1994 | Eberbach |
| 5,366,504 | A | 11/1994 | Andersen et al. |
| 5,370,657 | A | 12/1994 | Irie |
| 5,375,612 | A | 12/1994 | Cottenceau et al. |
| 5,397,331 | A | 3/1995 | Himpens et al. |
| 5,397,355 | A | 3/1995 | Marin et al. |
| 5,409,444 | A | 4/1995 | Kensey et al. |
| 5,417,699 | A | 5/1995 | Klein et al. |
| 5,421,832 | A | 6/1995 | Lefebvre |
| 5,425,744 | A | 6/1995 | Fagan et al. |
| 5,427,119 | A | 6/1995 | Swartz et al. |
| 5,433,727 | A | 7/1995 | Sideris |
| 5,443,454 | A | 8/1995 | Tanabe et al. |
| 5,443,478 | A | 8/1995 | Purdy et al. |
| 5,451,235 | A | 9/1995 | Lock et al. |
| 5,454,365 | A | 10/1995 | Bonutti |
| 5,464,408 | A | 11/1995 | Duc |
| 5,469,867 | A | 11/1995 | Schmitt |
| 5,490,856 | A | 2/1996 | Person et al. |
| 5,497,774 | A | 3/1996 | Swartz et al. |
| 5,499,975 | A | 3/1996 | Cope et al. |
| 5,499,995 | A | 3/1996 | Teirstein |
| 5,522,790 | A | 6/1996 | Voll et al. |
| 5,522,822 | A | 6/1996 | Phelps et al. |
| 5,522,836 | A | 6/1996 | Palermo |
| 5,527,322 | A | 6/1996 | Klein et al. |
| 5,527,338 | A | 6/1996 | Purdy |
| 5,558,093 | A | 9/1996 | Pomeranz et al. |
| 5,558,652 | A | 9/1996 | Henke |
| 5,569,204 | A | 10/1996 | Cramer et al. |
| 5,591,196 | A | 1/1997 | Marin et al. |
| 5,614,204 | A | 3/1997 | Cochrum |
| 5,634,936 | A | 6/1997 | Linden et al. |
| 5,634,942 | A | 6/1997 | Chevillon et al. |
| 5,637,097 | A | 6/1997 | Yoon |
| 5,643,282 | A | 7/1997 | Kieturakis |
| 5,643,292 | A | 7/1997 | Hart |
| 5,649,953 | A | 7/1997 | Lefebvre |
| 5,653,690 | A | 8/1997 | Booth et al. |
| 5,662,671 | A | 9/1997 | Barbut et al. |
| 5,669,933 | A | 9/1997 | Simon et al. |
| 5,681,345 | A | 10/1997 | Euteneuer |
| 5,681,347 | A | 10/1997 | Cathcart et al. |
| 5,683,411 | A | 11/1997 | Kavteladze et al. |
| 5,690,671 | A | 11/1997 | McGurk et al. |
| 5,693,067 | A | 12/1997 | Purdy |
| 5,695,525 | A | 12/1997 | Mulhauser et al. |
| 5,700,285 | A | 12/1997 | Myers et al. |
| 5,702,421 | A | 12/1997 | Schneidt |
| 5,704,910 | A | 1/1998 | Humes |
| 5,709,224 | A | 1/1998 | Behl et al. |
| 5,709,704 | A | 1/1998 | Nott et al. |
| 5,709,707 | A | 1/1998 | Lock et al. |
| 5,722,400 | A | 3/1998 | Ockuly et al. |
| 5,724,975 | A | 3/1998 | Negus et al. |
| 5,725,512 | A | 3/1998 | Swartz et al. |
| 5,725,552 | A | 3/1998 | Kotula et al. |
| 5,725,568 | A | 3/1998 | Hastings |
| 5,733,294 | A | 3/1998 | Forber et al. |
| 5,733,302 | A | 3/1998 | Myler et al. |
| 5,733,325 | A | 3/1998 | Robinson et al. |
| 5,735,290 | A | 4/1998 | Sterman et al. |
| 5,749,880 | A | 5/1998 | Banas et al. |
| 5,749,883 | A | 5/1998 | Halpern |
| 5,749,894 | A | 5/1998 | Engelson |
| 5,766,219 | A | 6/1998 | Horton |
| 5,766,246 | A | 6/1998 | Mulhauser et al. |
| 5,769,816 | A | 6/1998 | Barbut et al. |
| 5,776,097 | A | 7/1998 | Massoud |
| 5,776,162 | A | 7/1998 | Kleshinski |
| 5,782,860 | A | 7/1998 | Epstein et al. |
| 5,785,679 | A | 7/1998 | Abolfathi et al. |
| 5,800,454 | A | 9/1998 | Jacobsen et al. |
| 5,800,457 | A | 9/1998 | Gelbfish |
| 5,800,512 | A | 9/1998 | Letnz et al. |

(56) References Cited

U.S. PATENT DOCUMENTS 5,800,526 A 9/1998 Anderson et al.
5,807,261 A 9/1998 Benaron et al.
5,810,874 A 9/1998 Lefebvre
5,814,028 A 9/1998 Swartz et al.
5,814,029 A 9/1998 Hassett
5,814,064 A 9/1998 Daniel
5,820,591 A 10/1998 Thompson et al.
5,823,198 A 10/1998 Jones et al.
5,830,228 A 11/1998 Knapp et al.
5,833,673 A 11/1998 Ockuly et al.
5,836,913 A 11/1998 Orth et al.
5,836,968 A 11/1998 Simon et al.
5,840,027 A 11/1998 Swartz et al.
5,843,118 A 12/1998 Sepetka et al.
5,846,260 A 12/1998 Maahs
5,846,261 A 12/1998 Kotula et al.
5,848,969 A 12/1998 Panescu et al.
5,849,005 A 12/1998 Garrison et al.
5,851,232 A 12/1998 Lois
5,853,422 A 12/1998 Huebsch et al.
5,855,597 A 1/1999 Jayaraman
5,865,791 A 2/1999 Whayne et al.
5,865,802 A 2/1999 Yoon et al.
5,868,702 A 2/1999 Stevens et al.
5,868,708 A 2/1999 Hart et al.
5,876,367 A 3/1999 Kaganov et al.
5,879,296 A 3/1999 Ockuly et al.
5,879,366 A 3/1999 Shaw et al.
5,882,340 A 3/1999 Yoon
5,885,258 A 3/1999 Sachdeva et al.
5,891,558 A 4/1999 Bell et al.
5,895,399 A 4/1999 Barbut et al.
5,902,289 A 5/1999 Swartz et al.
5,904,680 A 5/1999 Kordis et al.
5,904,703 A 5/1999 Gilson
5,906,207 A 5/1999 Shen
5,910,154 A 6/1999 Tsugita et al.
5,911,734 A 6/1999 Tsugita et al.
5,916,236 A 6/1999 Muij Van de Moer et al.
5,925,060 A 7/1999 Forber
5,925,063 A 7/1999 Khosravi
5,925,074 A 7/1999 Gingras et al.
5,925,075 A 7/1999 Myers et al.
5,928,192 A 7/1999 Maahs
5,928,260 A 7/1999 Chin et al.
5,931,818 A 8/1999 Werp et al.
5,935,145 A 8/1999 Villar et al.
5,935,147 A 8/1999 Kensey et al.
5,935,148 A 8/1999 Villar et al.
5,941,249 A 8/1999 Maynard
5,941,896 A 8/1999 Kerr
5,944,738 A 8/1999 Amplatz et al.
5,947,997 A 9/1999 Pavcnik et al.
5,951,589 A 9/1999 Epstein et al.
5,951,599 A 9/1999 McCrory
5,954,694 A 9/1999 Sunseri
5,954,767 A 9/1999 Pajotin et al.
5,957,940 A 9/1999 Tanner et al.
5,961,545 A 10/1999 Lentz et al.
5,976,174 A 11/1999 Ruiz
5,980,514 A 11/1999 Kupiecki et al.
5,980,555 A 11/1999 Barbut et al.
5,989,281 A 11/1999 Barbut et al.
5,993,469 A 11/1999 McKenzie et al.
5,993,483 A 11/1999 Gianotti
5,997,557 A 12/1999 Barbut et al.
6,004,280 A 12/1999 Buck et al.
6,004,348 A 12/1999 Banas et al.
6,007,523 A 12/1999 Mangosong
6,007,557 A 12/1999 Ambrisco et al.
6,010,517 A 1/2000 Baccaro
6,010,522 A 1/2000 Barbut et al.
6,013,093 A 1/2000 Nott et al.
6,024,751 A 2/2000 Lovato et al.
6,024,754 A 2/2000 Engelson
6,024,755 A 2/2000 Addis
6,024,756 A 2/2000 Huebsch et al.
6,027,520 A 2/2000 Tsugita et al.
6,033,420 A 3/2000 Hahnen
6,036,720 A 3/2000 Abrams et al.
6,042,598 A 3/2000 Tsugita et al.
6,048,331 A 4/2000 Tsugita et al.
6,051,014 A 4/2000 Jang
6,051,015 A 4/2000 Maahs
6,056,720 A 5/2000 Morse
6,063,070 A 5/2000 Eder
6,063,113 A 5/2000 Kavteladze et al.
6,066,126 A 5/2000 Li et al.
6,068,621 A 5/2000 Balceta et al.
6,074,357 A 6/2000 Kaganov et al.
6,076,012 A 6/2000 Swanson et al.
6,079,414 A 6/2000 Roth
6,080,182 A 6/2000 Shaw et al.
6,080,183 A 6/2000 Tsugita et al.
6,083,239 A 7/2000 Addis
6,090,084 A 7/2000 Hassett et al.
6,096,052 A 8/2000 Callister et al.
6,096,053 A 8/2000 Bates et al.
6,110,243 A 8/2000 Wnenchak et al.
6,123,715 A 9/2000 Amplatz
6,124,523 A 9/2000 Banas et al.
6,132,438 A 10/2000 Fleischman et al.
6,135,991 A 10/2000 Muni et al.
6,136,016 A 10/2000 Barbut et al.
6,139,527 A 10/2000 Laufer et al.
6,139,573 A 10/2000 Sogard et al.
6,152,144 A 11/2000 Lesh et al.
6,152,946 A 11/2000 Broome et al.
6,156,055 A 12/2000 Ravenscroft
6,159,195 A 12/2000 Ha et al.
6,161,543 A 12/2000 Cox et al.
6,168,615 B1 1/2001 Ken et al.
6,171,329 B1 1/2001 Shaw et al.
6,179,859 B1 1/2001 Bates et al.
6,193,739 B1 2/2001 Chevillon et al.
6,203,531 B1 3/2001 Ockuly et al.
6,206,907 B1 3/2001 Marino et al.
6,214,029 B1 4/2001 Thill et al.
6,221,092 B1 4/2001 Koike et al.
6,231,561 B1 5/2001 Frazier et al.
6,231,589 B1 5/2001 Wessman et al.
6,235,045 B1 5/2001 Barbut et al.
6,245,012 B1 6/2001 Kleshinski
6,251,122 B1 6/2001 Tsukernik
6,258,115 B1 7/2001 Dubrul
6,267,772 B1 7/2001 Mulhauser et al.
6,267,776 B1 7/2001 O'Connell
6,270,490 B1 8/2001 Hahnen
6,270,530 B1 8/2001 Eldridge et al.
6,270,902 B1 8/2001 Tedeschi et al.
6,277,138 B1 8/2001 Levinson et al.
6,285,898 B1 9/2001 Ben-Haim
6,290,674 B1 9/2001 Roue et al.
6,290,708 B1 9/2001 Kugel et al.
6,312,407 B1 11/2001 Zadno-Azizi et al.
6,319,251 B1 11/2001 Tu et al.
6,328,727 B1 12/2001 Frazier et al.
6,328,755 B1 12/2001 Marshall
6,342,062 B1 1/2002 Suon et al.
6,346,116 B1 2/2002 Brooks et al.
6,346,895 B1 2/2002 Lee et al.
6,361,545 B1 3/2002 Macoviak et al.
6,364,895 B1 4/2002 Greenhalgh
6,368,338 B1 4/2002 Konya et al.
6,371,971 B1 4/2002 Tsugita et al.
6,375,670 B1 4/2002 Greenhalgh
6,391,044 B1 5/2002 Yadav et al.
6,398,803 B1 6/2002 Layne et al.
6,402,746 B1 6/2002 Whayne et al.
6,402,771 B1 6/2002 Palmer et al.
6,402,779 B1 6/2002 Colone et al.
6,419,669 B1 7/2002 Frazier et al.
6,440,152 B1 8/2002 Gainor et al.
6,443,972 B1 9/2002 Bosma et al.

(56) References Cited

U.S. PATENT DOCUMENTS

| | | | |
|---|---|---|---|
| 6,447,530 | B1 | 9/2002 | Ostrovsky et al. |
| 6,454,775 | B1 | 9/2002 | Demarais et al. |
| 6,458,145 | B1 | 10/2002 | Ravenscroft et al. |
| 6,464,712 | B1 | 10/2002 | Epstein et al. |
| 6,468,291 | B2 | 10/2002 | Bates et al. |
| 6,468,301 | B1 | 10/2002 | Amplatz et al. |
| 6,485,501 | B1 | 11/2002 | Green |
| 6,488,689 | B1 | 12/2002 | Kaplan et al. |
| 6,511,496 | B1 | 1/2003 | Huter et al. |
| 6,514,280 | B1 | 2/2003 | Gilson |
| 6,517,573 | B1 | 2/2003 | Pollock et al. |
| 6,533,782 | B2 | 3/2003 | Howell et al. |
| 6,547,760 | B1 | 4/2003 | Samson et al. |
| 6,547,815 | B2 | 4/2003 | Myers |
| 6,551,303 | B1 | 4/2003 | Van Tassel et al. |
| 6,551,344 | B2 | 4/2003 | Thill |
| 6,558,401 | B1 | 5/2003 | Azizi |
| 6,558,405 | B1 | 5/2003 | McInnes |
| 6,558,414 | B2 | 5/2003 | Layne |
| 6,562,058 | B2 | 5/2003 | Seguin et al. |
| 6,569,184 | B2 | 5/2003 | Huter |
| 6,569,214 | B2 | 5/2003 | Williams et al. |
| 6,589,214 | B2 | 7/2003 | McGuckin et al. |
| 6,589,251 | B2 | 7/2003 | Yee et al. |
| 6,599,308 | B2 | 7/2003 | Amplatz |
| 6,602,271 | B2 | 8/2003 | Adams et al. |
| 6,623,508 | B2 | 9/2003 | Shaw et al. |
| 6,641,564 | B1 | 11/2003 | Kraus |
| 6,650,923 | B1 | 11/2003 | Lesh et al. |
| 6,652,555 | B1 | 11/2003 | VanTassel et al. |
| 6,652,556 | B1 | 11/2003 | VanTassel et al. |
| 6,666,861 | B1 | 12/2003 | Grabek |
| 6,689,150 | B1 | 2/2004 | Vantassel et al. |
| 6,699,260 | B2 | 3/2004 | Dubrul et al. |
| 6,699,276 | B2 | 3/2004 | Sogard et al. |
| 6,702,825 | B2 | 3/2004 | Frazier et al. |
| 6,712,836 | B1 | 3/2004 | Berg et al. |
| 6,726,701 | B2 | 4/2004 | Gilson et al. |
| 6,730,108 | B2 | 5/2004 | Van Tassel et al. |
| 6,755,812 | B2 | 6/2004 | Peterson et al. |
| 6,827,737 | B2 | 12/2004 | Hill et al. |
| 6,837,901 | B2 | 1/2005 | Rabkin et al. |
| 6,855,153 | B2 | 2/2005 | Saadat |
| 6,911,037 | B2 | 6/2005 | Gainor et al. |
| 6,932,838 | B2 | 8/2005 | Schwartz et al. |
| 6,942,653 | B2 | 9/2005 | Quinn |
| 6,949,113 | B2 | 9/2005 | Van Tassel et al. |
| 6,958,061 | B2 | 10/2005 | Truckai et al. |
| 6,994,092 | B2 | 2/2006 | van der Burg et al. |
| 7,011,671 | B2 | 3/2006 | Welch |
| 7,014,645 | B2 | 3/2006 | Greene, Jr. et al. |
| 7,037,321 | B2 | 5/2006 | Sachdeva et al. |
| 7,044,134 | B2 | 5/2006 | Khairkhahan et al. |
| 7,097,651 | B2 | 8/2006 | Harrison et al. |
| 7,128,073 | B1 | 10/2006 | van der Burg et al. |
| 7,152,605 | B2 | 12/2006 | Khairkhahan et al. |
| 7,169,164 | B2 | 1/2007 | Borillo et al. |
| 7,179,275 | B2 | 2/2007 | McGuckin, Jr. et al. |
| 7,226,466 | B2 | 6/2007 | Opolski |
| 7,303,526 | B2 | 12/2007 | Sharkey et al. |
| 7,323,002 | B2 | 1/2008 | Johnson et al. |
| 7,597,704 | B2 | 10/2009 | Frazier et al. |
| 7,678,123 | B2 | 3/2010 | Chanduszko |
| 7,695,425 | B2 | 4/2010 | Schweich et al. |
| 7,713,282 | B2 | 5/2010 | Frazier et al. |
| 7,722,641 | B2 | 5/2010 | van der Burg et al. |
| 7,727,189 | B2 | 6/2010 | VanTassel et al. |
| 7,735,493 | B2 | 6/2010 | van der Burg et al. |
| 7,748,389 | B2 | 7/2010 | Salahieh et al. |
| 7,780,694 | B2 | 8/2010 | Palmer et al. |
| 7,794,472 | B2 | 9/2010 | Eidenschink et al. |
| 7,799,049 | B2 | 9/2010 | Ostrovsky et al. |
| 7,803,171 | B1 | 9/2010 | Uflacker |
| 7,811,300 | B2 | 10/2010 | Feller, III et al. |
| 7,811,314 | B2 | 10/2010 | Fierens et al. |
| 7,862,500 | B2 | 1/2011 | Khairkhahan et al. |
| 7,927,365 | B2 | 4/2011 | Fierens et al. |
| 7,959,645 | B2 | 6/2011 | WasDyke et al. |
| 7,972,359 | B2 | 7/2011 | Kreidler |
| 8,025,495 | B2 | 9/2011 | Hardert et al. |
| 8,043,329 | B2 | 10/2011 | Khairkhahan et al. |
| 8,052,715 | B2 | 11/2011 | Quinn et al. |
| 8,062,282 | B2 | 11/2011 | Kolb |
| 8,080,032 | B2 | 12/2011 | van der Burg et al. |
| 8,097,015 | B2 | 1/2012 | Devellian |
| 8,173,062 | B1 * | 5/2012 | Durcan .................. B29C 49/04 264/249 |
| 8,221,384 | B2 | 7/2012 | Frazier et al. |
| 8,221,445 | B2 | 7/2012 | van Tassel et al. |
| 8,246,648 | B2 | 8/2012 | Tekulve |
| 8,287,563 | B2 | 10/2012 | Khairkhahan et al. |
| 8,323,309 | B2 | 12/2012 | Khairkhahan et al. |
| 8,372,143 | B2 | 2/2013 | Majercak et al. |
| 8,388,672 | B2 | 3/2013 | Khairkhahan et al. |
| 8,491,623 | B2 | 7/2013 | Vogel et al. |
| 8,523,897 | B2 | 9/2013 | van der Burg et al. |
| 8,535,343 | B2 | 9/2013 | van der Burg et al. |
| 8,562,509 | B2 | 10/2013 | Bates |
| 8,663,273 | B2 | 3/2014 | Khairkhahan et al. |
| 8,685,055 | B2 | 4/2014 | VanTassel et al. |
| 8,740,931 | B2 | 6/2014 | Snow |
| 8,834,519 | B2 | 9/2014 | van der Burg et al. |
| 8,845,711 | B2 | 9/2014 | Miles et al. |
| 8,998,944 | B2 | 4/2015 | Thornton |
| 9,034,006 | B2 | 5/2015 | Quinn et al. |
| 9,132,000 | B2 | 9/2015 | VanTassel et al. |
| 9,168,043 | B2 | 10/2015 | van der Burg et al. |
| 9,186,152 | B2 | 11/2015 | Campbell et al. |
| 9,211,124 | B2 | 12/2015 | Campbell et al. |
| 9,445,895 | B2 | 9/2016 | Kreidler |
| 9,554,806 | B2 | 1/2017 | Larsen et al. |
| 9,561,037 | B2 | 2/2017 | Fogarty et al. |
| 9,561,097 | B1 | 2/2017 | Kim et al. |
| 9,629,636 | B2 | 4/2017 | Fogarty et al. |
| 9,700,323 | B2 | 7/2017 | Clark |
| 9,724,121 | B2 * | 8/2017 | Hefer .................... A61M 29/02 |
| 9,730,701 | B2 | 8/2017 | Tischler et al. |
| 9,883,936 | B2 | 2/2018 | Sutton et al. |
| 9,913,652 | B2 | 3/2018 | Bridgeman et al. |
| 9,943,299 | B2 | 4/2018 | Khairkhahan et al. |
| 9,943,315 | B2 | 4/2018 | Kaplan et al. |
| 10,071,181 | B1 | 9/2018 | Penegor et al. |
| 10,076,335 | B2 | 9/2018 | Zaver et al. |
| 10,111,645 | B2 | 10/2018 | Fearnot et al. |
| 10,143,458 | B2 | 12/2018 | Kreidler |
| 10,258,454 | B2 | 4/2019 | Molgaard-Nielsen et al. |
| 10,603,020 | B2 | 3/2020 | Rudman et al. |
| 10,939,986 | B2 | 3/2021 | Chen et al. |
| 11,039,822 | B2 | 6/2021 | Wang et al. |
| 2001/0000797 | A1 | 5/2001 | Mazzocchi |
| 2001/0020181 | A1 | 9/2001 | Ayne |
| 2001/0034537 | A1 | 10/2001 | Shaw et al. |
| 2001/0037141 | A1 | 11/2001 | Yee et al. |
| 2002/0022860 | A1 | 2/2002 | Borillo et al. |
| 2002/0035374 | A1 | 3/2002 | Borillo et al. |
| 2002/0045931 | A1 | 4/2002 | Sogard et al. |
| 2002/0062133 | A1 | 5/2002 | Gilson et al. |
| 2002/0082638 | A1 | 6/2002 | Porter et al. |
| 2002/0082675 | A1 | 6/2002 | Myers |
| 2002/0099439 | A1 | 7/2002 | Schwartz et al. |
| 2002/0111647 | A1 | 8/2002 | Khairkhahan et al. |
| 2002/0138094 | A1 | 9/2002 | Borillo et al. |
| 2002/0138097 | A1 | 9/2002 | Ostrovsky et al. |
| 2002/0169475 | A1 | 11/2002 | Gainor et al. |
| 2002/0177855 | A1 | 11/2002 | Greene, Jr. et al. |
| 2003/0017775 | A1 | 1/2003 | Dong et al. |
| 2003/0023262 | A1 | 1/2003 | Welch |
| 2003/0023266 | A1 | 1/2003 | Borillo et al. |
| 2003/0057156 | A1 | 3/2003 | Peterson et al. |
| 2003/0060871 | A1 | 3/2003 | Hill et al. |
| 2003/0120337 | A1 | 6/2003 | Van Tassel et al. |
| 2003/0181942 | A1 | 9/2003 | Sutton et al. |
| 2003/0191526 | A1 | 10/2003 | Van Tassel et al. |
| 2003/0195555 | A1 | 10/2003 | Khairkhahan et al. |

(56) References Cited

U.S. PATENT DOCUMENTS

2003/0204203 A1 10/2003 Khairkhahan et al.
2003/0208214 A1 11/2003 Loshakove et al.
2003/0220667 A1 11/2003 van der Burg et al.
2004/0034366 A1 2/2004 van der Burg et al.
2004/0049210 A1 3/2004 VanTassel et al.
2004/0093012 A1 5/2004 Cully et al.
2004/0098031 A1 5/2004 van der Burg et al.
2004/0117004 A1 6/2004 Osborne et al.
2004/0122467 A1 6/2004 VanTassel et al.
2004/0127935 A1 7/2004 VanTassel et al.
2004/0158274 A1 8/2004 WasDyke
2004/0186486 A1 9/2004 Roue et al.
2004/0215230 A1 10/2004 Frazier et al.
2004/0220610 A1 11/2004 Kreidler et al.
2004/0220682 A1 11/2004 Levine et al.
2004/0230222 A1 11/2004 van der Burg et al.
2005/0004652 A1 1/2005 van der Burg et al.
2005/0015109 A1 1/2005 Lichtenstein
2005/0038470 A1 2/2005 van der Burg et al.
2005/0049573 A1 3/2005 Van Tassel et al.
2005/0070952 A1 3/2005 Devellian
2005/0113861 A1 5/2005 Corcoran et al.
2005/0125020 A1 6/2005 Meade et al.
2005/0177182 A1 8/2005 van der Burg et al.
2005/0203568 A1 9/2005 Burg et al.
2005/0283186 A1 12/2005 Berrada et al.
2005/0288704 A1 12/2005 Cartier et al.
2006/0015136 A1 1/2006 Besselink
2006/0030877 A1 2/2006 Martinez et al.
2006/0052816 A1 3/2006 Bates et al.
2006/0100658 A1 5/2006 Obana et al.
2006/0155323 A1 7/2006 Porter et al.
2007/0066993 A1 3/2007 Kreidler
2007/0083227 A1 4/2007 van der Burg et al.
2007/0083230 A1 4/2007 Javois
2007/0150041 A1 6/2007 Evans et al.
2007/0156123 A1 7/2007 Moll et al.
2007/0162048 A1 7/2007 Quinn et al.
2007/0185471 A1 8/2007 Johnson
2008/0275536 A1 11/2008 Zarins et al.
2009/0005803 A1 1/2009 Batiste
2009/0062841 A1 3/2009 Amplatz et al.
2009/0099647 A1 4/2009 Glimsdale et al.
2009/0105747 A1 4/2009 Chanduszko et al.
2009/0112249 A1 4/2009 Miles et al.
2009/0149945 A1 6/2009 Pike
2009/0171386 A1 7/2009 Amplatz et al.
2009/0254195 A1 10/2009 Khairkhan et al.
2009/0270972 A1 10/2009 Lane
2009/0318948 A1 12/2009 Linder et al.
2010/0004726 A1 1/2010 Hancock et al.
2010/0016953 A1 1/2010 Sisken et al.
2010/0049238 A1 2/2010 Simpson
2010/0106178 A1 4/2010 Obermiller et al.
2010/0256669 A1 10/2010 Harris et al.
2010/0324585 A1 12/2010 Miles et al.
2011/0054515 A1 3/2011 Bridgeman et al.
2011/0082495 A1 4/2011 Ruiz
2011/0098525 A1 4/2011 Kermode et al.
2011/0218566 A1 9/2011 van der Burg et al.
2011/0301630 A1 12/2011 Hendriksen et al.
2012/0029553 A1 2/2012 Quinn et al.
2012/0035643 A1 2/2012 Khairkhahan et al.
2012/0065662 A1 3/2012 van der Burg et al.
2012/0125619 A1 5/2012 Wood et al.
2012/0172654 A1 7/2012 Bates
2012/0172927 A1 7/2012 Campbell et al.
2012/0191174 A1 7/2012 Vinluan et al.
2012/0239077 A1 9/2012 Zaver et al.
2012/0239083 A1 9/2012 Kreidler
2012/0245619 A1 9/2012 Guest
2012/0283585 A1 11/2012 Werneth et al.
2012/0283773 A1 11/2012 Van Tassel et al.
2012/0323267 A1 12/2012 Ren
2013/0006343 A1 1/2013 Kassab et al.
2013/0012982 A1 1/2013 Khairkhahan et al.
2013/0018413 A1 1/2013 Oral et al.
2013/0110154 A1 5/2013 van der Burg et al.
2013/0131717 A1 5/2013 Glimsdale
2013/0165735 A1 6/2013 Khairkhahan et al.
2013/0178889 A1 7/2013 Miles et al.
2013/0211492 A1 8/2013 Schneider et al.
2013/0331884 A1 12/2013 Van der Burg et al.
2014/0005714 A1 1/2014 Quick et al.
2014/0018841 A1 1/2014 Peiffer et al.
2014/0039536 A1 2/2014 Cully et al.
2014/0046360 A1 2/2014 van der Burg et al.
2014/0081314 A1 3/2014 Zaver et al.
2014/0100596 A1 4/2014 Rudman et al.
2014/0142612 A1 5/2014 Li et al.
2014/0148842 A1 5/2014 Khairkhahan et al.
2014/0163605 A1 6/2014 VanTassel et al.
2014/0188157 A1 7/2014 Clark
2014/0277562 A1* 9/2014 Seddon .................. A61F 2/915
219/121.72
2014/0303719 A1 10/2014 Cox et al.
2014/0336612 A1 11/2014 Frydlewski et al.
2014/0336699 A1 11/2014 van der Burg et al.
2015/0005810 A1 1/2015 Center et al.
2015/0039021 A1 2/2015 Khairkhahan et al.
2015/0080903 A1 3/2015 Dillard et al.
2015/0196300 A1 7/2015 Tischler et al.
2015/0230909 A1 8/2015 Zaver et al.
2015/0238197 A1 8/2015 Quinn et al.
2015/0305727 A1 10/2015 Karimov et al.
2015/0313604 A1 11/2015 Roue et al.
2015/0313605 A1 11/2015 Griffin
2015/0327979 A1 11/2015 Quinn et al.
2015/0374491 A1 12/2015 Kreidler
2016/0051358 A1 2/2016 Sutton et al.
2016/0058539 A1 3/2016 VanTassel et al.
2016/0066922 A1 3/2016 Bridgeman et al.
2016/0106437 A1 4/2016 van der Burg et al.
2016/0192942 A1 7/2016 Strauss et al.
2016/0287259 A1 10/2016 Hanson et al.
2016/0331382 A1 11/2016 Center et al.
2016/0374657 A1 12/2016 Kreidler
2017/0027552 A1 2/2017 Turkington et al.
2017/0042550 A1 2/2017 Chakraborty et al.
2017/0056166 A1 3/2017 Ratz et al.
2017/0100112 A1 4/2017 van der Burg et al.
2017/0119400 A1 5/2017 Amplatz et al.
2017/0181751 A1 6/2017 Larsen et al.
2017/0340336 A1 11/2017 Osypka
2018/0064446 A1 3/2018 Figulla et al.
2018/0070950 A1 3/2018 Zaver et al.
2018/0140412 A1 5/2018 Sutton et al.
2018/0140413 A1 5/2018 Quinn et al.
2018/0250014 A1 9/2018 Melanson et al.
2018/0310925 A1 11/2018 Inouye et al.
2019/0046213 A1 2/2019 Gong et al.
2019/0083224 A1 3/2019 Tessmer
2019/0117367 A1 4/2019 Simpson
2019/0125362 A1 5/2019 Tischler
2019/0167242 A1 6/2019 Rowe et al.
2019/0223883 A1 7/2019 Anderson et al.
2019/0298380 A1 10/2019 Inouye et al.
2019/0299011 A1 10/2019 Chu
2020/0008812 A1 1/2020 Inouye et al.
2020/0060801 A1 2/2020 Yang
2020/0060849 A1 2/2020 Inouye et al.
2020/0178981 A1 6/2020 Anderson et al.
2021/0015596 A1 1/2021 Nigon
2021/0059685 A1 3/2021 Groff et al.

FOREIGN PATENT DOCUMENTS

CN 106859722 A 6/2017
DE 10201004476 A1 3/2012
EP 1523957 A2 4/2005
EP 1595504 A1 11/2005
EP 2074953 A1 1/2009
EP 2481381 A1 8/2012
EP 2928420 A1 10/2015

(56) References Cited

FOREIGN PATENT DOCUMENTS

| | | | |
|---|---|---|---|
| EP | 3072461 | A1 | 9/2016 |
| EP | 3372173 | A2 | 9/2018 |
| EP | 3494902 | A1 | 6/2019 |
| JP | 2003532457 | A | 11/2003 |
| JP | 2005324019 | A | 11/2005 |
| JP | 2007513684 | A | 5/2007 |
| JP | 2009160402 | A | 7/2009 |
| JP | 2012501793 | A | 1/2012 |
| WO | 9313712 | A1 | 7/1993 |
| WO | 9504132 | A1 | 2/1995 |
| WO | 9522359 | A1 | 8/1995 |
| WO | 9601591 | A1 | 1/1996 |
| WO | 9640356 | A1 | 12/1996 |
| WO | 9721402 | A1 | 6/1997 |
| WO | 9726939 | A1 | 7/1997 |
| WO | 9728749 | A1 | 8/1997 |
| WO | 9735522 | A1 | 10/1997 |
| WO | 9802100 | A1 | 1/1998 |
| WO | 9817187 | A1 | 4/1998 |
| WO | 9822026 | A1 | 5/1998 |
| WO | 9823322 | A1 | 6/1998 |
| WO | 9827868 | A1 | 7/1998 |
| WO | 9905977 | A1 | 2/1999 |
| WO | 9907289 | A1 | 2/1999 |
| WO | 9908607 | A1 | 2/1999 |
| WO | 9923976 | A1 | 5/1999 |
| WO | 9925252 | A1 | 5/1999 |
| WO | 9930640 | A1 | 6/1999 |
| WO | 9944510 | A1 | 9/1999 |
| WO | 9959479 | A1 | 11/1999 |
| WO | 0001308 | A1 | 1/2000 |
| WO | 0016705 | A1 | 3/2000 |
| WO | 0027292 | A1 | 5/2000 |
| WO | 0035352 | A1 | 6/2000 |
| WO | 0053120 | A1 | 9/2000 |
| WO | 0067669 | A1 | 11/2000 |
| WO | 0108743 | A1 | 2/2001 |
| WO | 0115629 | A1 | 3/2001 |
| WO | 0121247 | A1 | 3/2001 |
| WO | 0126726 | A1 | 4/2001 |
| WO | 0130266 | A1 | 5/2001 |
| WO | 0130267 | A1 | 5/2001 |
| WO | 0130268 | A1 | 5/2001 |
| WO | 0170119 | A1 | 9/2001 |
| WO | 0215793 | A2 | 2/2002 |
| WO | 0224106 | A2 | 3/2002 |
| WO | 02071977 | A2 | 9/2002 |
| WO | 03007825 | A1 | 1/2003 |
| WO | 03008030 | A2 | 1/2003 |
| WO | 03032818 | A1 | 4/2003 |
| WO | 2004012629 | A1 | 2/2004 |
| WO | 2007044536 | A1 | 4/2007 |
| WO | 2010024801 | A1 | 3/2010 |
| WO | 2010081033 | A1 | 7/2010 |
| WO | 2013060855 | A1 | 5/2013 |
| WO | 2013159065 | A1 | 10/2013 |
| WO | 2014011865 | A1 | 1/2014 |
| WO | 2014018907 | A1 | 1/2014 |
| WO | 2014078698 | A2 | 5/2014 |
| WO | 2014089129 | A1 | 6/2014 |
| WO | 2014106239 | A1 | 7/2014 |
| WO | 2015164836 | A1 | 10/2015 |
| WO | 2016087145 | A1 | 6/2016 |
| WO | 2018017935 | A1 | 1/2018 |
| WO | 2018187732 | A1 | 10/2018 |
| WO | 2019084358 | A1 | 5/2019 |
| WO | 2021052486 | A1 | 3/2021 |

OTHER PUBLICATIONS

International Search Report and Written Opinion dated Feb. 15, 2000 for International Application No. PCT/US99/26325.

International Search Report dated May 20, 2003 for International Application No. PCT/US02/33808.

Written Opinion dated Nov. 17, 2003 for International Application No. PCT/US/02/33808.

International Search Report and Written Opinion dated Aug. 21, 2018 for International Application No. PCT/US2018/029684.

Cragg et al., "A New Percutaneous Vena Cava Filter," American Journal of Radiology, Sep. 1983, pp. 601-604, vol. 141.

Cragg et al., "Nonsurgical Placement of Arterial Endoprostheses: A New Technique Using Nitinol Wire," Radiology, Apr. 1983, pp. 261-263, vol. 147, No. 1.

Lock et al., "Transcatheter Closure of Atrial Septal Defects." Circulation, May 1989, pp. 1091-1099, vol. 79, No. 5.

Lock et al., "Transcatheter Umbrella Closure of Congenital Heart Defects," Circulation, Mar. 1987, pp. 593-599, vol. 75, No. 3.

Rashkind et al., "Nonsurgical closure of patent ductus arteriosus: clinical application of the Rashkind PDA Occluder System," Circulation, Mar. 1987, pp. 583-592, vol. 75, No. 3.

Rosengart et al., "Percutaneous and Minimally Invasive Valve Procedures," Circulation, Apr. 1, 2008, pp. 1750-1767, vol. 117.

Ruttenberg, "Nonsurgical Therapy of Cardiac Disorders," Pediatric Consult, 1986, Pages not numbered, vol. 5, No. 2.

Sugita et al., "Nonsurgical Implantations of a Vascular Ring Prosthesis Using Thermal Shape Memory Ti/Ni Alloy (Nitinol Wire)," Trans. Am. Soc. Artif. Intern. Organs, 1986, pp. 30-34, vol. XXXII.

Wessel et al., "Outpatient Closure of the Patent Ductus Arteriousus," Circulation, 1988, pp. 1068-1071, vol. 77, No. 5.

Tung et al., U.S. Appl. No. 61/559,941, filed Nov. 15, 2011.

Yue Yu et al., U.S. Appl. No. 61/557,880, filed Dec. 20, 2011.

Cline, "File: Fish hooks.jpg," Wikipedia foundation , Inc., San Francisco, CA, Jun. 2007; p. 1 of 4; available online at http://en.wikipedia.org/wiki/File:Fish_hooks.jpg; last accessed Oct. 5, 2012.

International Search Report and Written Opinion dated Apr. 22, 2014 for International Application No. PCT/US2013/078454.

Aryana et al., "Incomplete Closure of the Left Atrial Appendage: Implication and Management." Curr Cardiol Rep., 18(9):82, 2016.

Delurgio, "Device-Associated Thrombus and Peri-Device Leak Following Left Atrial Appendage Closure with the Amplatzer Cardiac Plug." JACC: Cardiovascular Interventions, 10(4): 400-402, 2017.

University of Minnesota. Atlas of Human Cardiac Anatomy, Left Atrium. Retrieved from http://www.vhlab.umn.edu/atlas/left-atrium/left-atrial-appendage/index.shtml. Accessed 2017. Downloaded 2019.

Saw et al., "Incidence and Clinical Impact of Device-Associated Thrombus and Peri-Device Leak following Left Atrial Appendage Closure with the Amplatzer Cardiac Plug." JACC: Cardiovascular Intervention. 10(4): 391-399, 2017.

Romero et al., "Left Atrial Appendage Closure Devices," Clinical Medicine Insights: Cardiology, vol. 8, pp. 45-52, 2014.

Invitation To Pay Additional Fees And, Where Applicable, Protest Fee, for International Application No. PCT/ US2016/043363, mailed Oct. 13, 2016.

International Search Report and Written Opinion dated Oct. 14, 2019 for International Application No. PCT/US2019/047452.

International Search Report and Written Opinion dated Oct. 27, 2017 for International Application No. PCT/US2017/048150.

International Search Report and Written Opinion dated Jan. 21, 2019 for International Application No. PCT/US2018/051953.

International Search Report and Written Opinion dated Oct. 13, 2016 for International Application No. PCT/US2016/043363.

International Search Report and Written Opinion dated Mar. 17, 2020, for International Application No. PCT/US2019/065243.

International Search Report and Written Opinion dated Sep. 9, 2019 for International Application No. PCT/US2019/033698.

Blackshear et al; "Appendage Obliteration to Reduce Stroke in Cardiac Surgical Patients with Atrial Fibrillation", Ann. Thoracic Surgery, pp. 755-759, 1996.

Lindsay, "Obliteration of the Left Atrial Appendage: A Concept Worth Testing", Ann. Thoracic Surgery, 1996.

Invitation To Pay Additional Fees dated Feb. 22, 2019 for International Application No. PCT/US2018/066163.

International Search Report and Written Opinion dated Oct. 23, 2020 for International Application No. PCT/US2020/042192.

International Search Report and Written Opinion dated Aug. 25, 2023 for International Application No. PCT/US2023/024824.

(56) References Cited

OTHER PUBLICATIONS

International Search Report and Written Opinion dated Feb. 23, 2023 for International Application No. PCT/US2022/049080.
International Search Report and Written Opinion dated Dec. 6, 2022 for International Application No. PCT/US2022/042696.
LabCE. https://www.labce.com/spg579126_red_blood_cell_rbc_size_variation.aspx. "Red Blood Cell (RBC) Size Variation", 2019.

* cited by examiner

MEDICAL IMPLANT AND METHODS OF MANUFACTURING THE MEDICAL IMPLANT

CROSS-REFERENCE TO RELATED APPLICATIONS

This application claims the benefit of priority of U.S. Provisional Application No. 63/350,520 filed Jun. 9, 2022, the entire disclosure of which is hereby incorporated by reference.

TECHNICAL FIELD

The present disclosure pertains to medical devices and systems, and methods for manufacturing and using medical devices and systems. More particularly, the present disclosure pertains to medical implants for occluding a left atrial appendage and methods of manufacturing the medical implants.

BACKGROUND

Diseases and/or medical conditions that impact the cardiovascular system are prevalent throughout the world. Traditionally, treatment of the cardiovascular system was often conducted by directly accessing the impacted part of the system. More recently, less invasive therapies have been developed, and have gained wide acceptance among patients and clinicians.

Atrial fibrillation a common sustained cardiac arrhythmia affecting over 30 million people worldwide, according to some estimates. Atrial fibrillation is the irregular, chaotic beating of the upper chambers of the heart. Electrical impulses discharge so rapidly that the atrial muscle quivers or fibrillates. Episodes of atrial fibrillation may last a few minutes or several days. The most serious consequence of atrial fibrillation is ischemic stroke. It has been estimated that up to 20% of all strokes are related to atrial fibrillation. Most atrial fibrillation patients, regardless of the severity of their symptoms or frequency of episodes, require treatment to reduce the risk of stroke. The left atrial appendage is a small organ attached to the left atrium of the heart as a pouch-like extension. In patients suffering from atrial fibrillation, the left atrial appendage may not properly contract with the left atrium, causing stagnant blood to pool within its interior, which can lead to the undesirable formation of thrombi within the left atrial appendage. Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation are found in the left atrial appendage. As a treatment, medical devices have been developed which are positioned in the left atrial appendage and deployed to close off the ostium of the left atrial appendage. Over time, the exposed surface(s) spanning the ostium of the left atrial appendage becomes covered with tissue (a process called endothelization), effectively removing the left atrial appendage from the circulatory system and reducing or eliminating the number of thrombi which may enter the blood stream from the left atrial appendage.

The disclosure relates to medical implants for occluding the left atrial appendage and/or methods of manufacturing the medical implants. Of the known medical devices, systems, and methods, each has certain advantages and disadvantages. There is an ongoing need to provide alternative medical devices and systems, as well as alternative methods for manufacturing and using medical devices and systems.

SUMMARY

In one example, a method of manufacturing a medical implant for occluding a left atrial appendage may comprise cutting an expandable scaffold in a first configuration, wherein the expandable scaffold includes a plurality of struts having ends joined together at intersection points and a plurality of anchor members extending from the plurality of struts such that each anchor member extends from a medial portion of a strut of the plurality of struts; forming the expandable scaffold into a second configuration, wherein forming the expandable scaffold into the second configuration includes bending each anchor member along its bending axis, the bending axis being oriented parallel to a longitudinal axis of its respective strut of the plurality of struts; and heat setting the expandable scaffold in the second configuration.

In additional or alternatively to any example described herein, the expandable scaffold is cut with a laser.

In additional or alternatively to any example described herein, the first configuration is a radially collapsed configuration and the second configuration is a radially expanded configuration.

In additional or alternatively to any example described herein, each anchor member extends radially outward from the plurality of struts after bending.

In additional or alternatively to any example described herein, forming the expandable scaffold into the second configuration includes preventing the plurality of struts from twisting.

In additional or alternatively to any example described herein, bending each anchor member includes preventing its respective strut from rotating about the longitudinal axis of the respective strut as the anchor member is bent.

In additional or alternatively to any example described herein, the expandable scaffold is formed from a unitary tubular member.

In additional or alternatively to any example described herein, bending each anchor member includes inserting a punch into an interior of the expandable scaffold, and moving the punch radially outward relative to the plurality of struts.

In additional or alternatively to any example described herein, moving the punch radially outward relative to the plurality of struts simultaneously bends more than one of the plurality of anchor members.

In additional or alternatively to any example described herein, bending each anchor member includes inserting a die into an interior of the expandable scaffold, positioning its respective strut over a groove formed in the die, and urging the respective strut into the groove with a punch.

In additional or alternatively to any example described herein, the expandable scaffold is formed from a flat sheet of material.

In additional or alternatively to any example described herein, bending each anchor member includes moving a punch through the expandable scaffold without moving the plurality of struts.

In additional or alternatively to any example described herein, bending each anchor member includes positioning its respective strut over a groove formed in a die, and urging the respective strut into the groove with a punch.

In additional or alternatively to any example described herein, the method may further comprise forming the flat sheet of material into a tubular member.

In additional or alternatively to any example described herein, a method of manufacturing a medical implant for occluding a left atrial appendage may comprise cutting an expandable scaffold in a first configuration, wherein the expandable scaffold includes a plurality of struts having ends joined together at intersection points and a plurality of anchor members extending from the plurality of struts such that each anchor member extends from a medial portion of a strut of the plurality of struts; forming the expandable scaffold into a second configuration, wherein forming the expandable scaffold into the second configuration includes bending each anchor member along its bending axis, the bending axis being oriented parallel to a longitudinal axis of its respective strut of the plurality of struts; heat setting the expandable scaffold in the second configuration; and securing an occlusive element to the expandable scaffold.

In additional or alternatively to any example described herein, at least some of the plurality of anchor members extend through the occlusive element in the second configuration.

In additional or alternatively to any example described herein, the occlusive element is disposed along an exterior surface of the expandable scaffold.

In additional or alternatively to any example described herein, the occlusive element covers at least 30% of the expandable scaffold in the second configuration.

In additional or alternatively to any example described herein, a medical implant for occluding a left atrial appendage may comprise an expandable scaffold configured to shift from a radially collapsed configuration to a radially expanded configuration. The expandable scaffold may include a plurality of struts having ends joined together at intersection points and a plurality of anchor members extending from the plurality of struts such that each anchor member extends from a medial portion of a strut of the plurality of struts. In the radially expanded configuration, each anchor member may have a bending axis oriented parallel to a longitudinal axis of its respective strut of the plurality of struts and each anchor member, and the plurality of anchor members may extend radially outward from the plurality of struts.

In additional or alternatively to any example described herein, each bending axis is oriented parallel to a central longitudinal axis of the expandable scaffold in the radially collapsed configuration.

The above summary of some embodiments, aspects, and/or examples is not intended to describe each disclosed embodiment or every implementation of the present disclosure. The figures and detailed description which follow more particularly exemplify these embodiments.

BRIEF DESCRIPTION OF THE DRAWINGS

The disclosure may be more completely understood in consideration of the following detailed description in connection with the accompanying drawings, in which.

Figure 1:
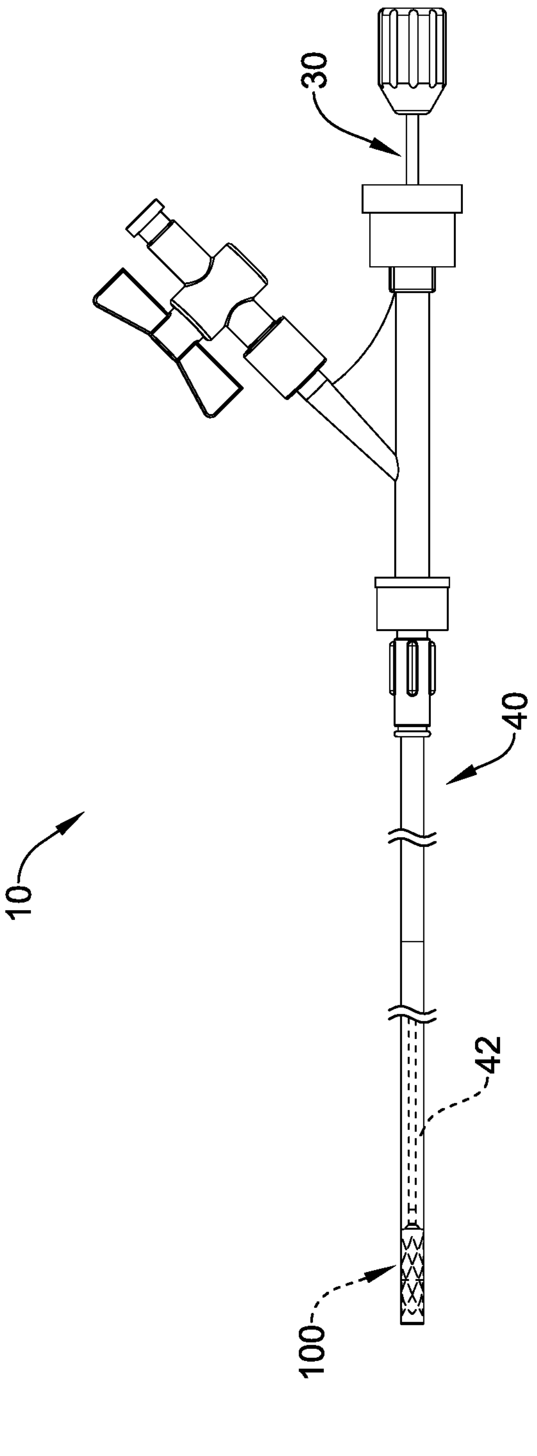
FIGS. 1-2 are side views of an example medical device system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the disclosure. Those skilled in the art will recognize that the various elements described and/or shown may be arranged in various combinations and configurations without departing from the scope of the disclosure. The detailed description and drawings illustrate exemplary aspects of the disclosure.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, all elements of the disclosure are not necessarily shown in each figure or discussed in detail below. However, it will be understood that the following discussion may apply equally to any and/or all of the components for which there are more than one, unless explicitly stated to the contrary.

Relative terms such as “proximal”, “distal”, “advance”, “retract”, variants thereof, and the like, may be generally considered with respect to the positioning, direction, and/or operation of various elements relative to a user/operator/manipulator of the device, wherein “proximal” and “retract” indicate or refer to closer to or toward the user and “distal” and “advance” indicate or refer to farther from or away from the user. In some instances, the terms “proximal” and “distal” may be arbitrarily assigned in an effort to facilitate understanding of the disclosure, and such instances will be readily apparent to the skilled artisan. Other relative terms, such as “upstream”, “downstream”, “inflow”, and “outflow” refer to a direction of fluid flow within a lumen, such as a body lumen, a blood vessel, or within a device. Still other relative terms, such as “axial”, “circumferential”, “longitudinal”, “lateral”, “radial”, etc. and/or variants thereof generally refer to direction and/or orientation relative to a central longitudinal axis of the disclosed structure or device.

The term “extent” may be understood to mean the greatest measurement of a stated or identified dimension, unless the extent or dimension in question is preceded by or identified as a “minimum”, which may be understood to mean the smallest measurement of the stated or identified dimension. For example, “outer extent” may be understood to mean a maximum outer dimension, “radial extent” may be understood to mean a maximum radial dimension, “longitudinal extent” may be understood to mean a maximum longitudinal dimension, etc. Each instance of an “extent” may be different (e.g., axial, longitudinal, lateral, radial, circumferential, etc.) and will be apparent to the skilled person from the context of the individual usage. Generally, an “extent” may be considered the greatest dimension measured according to the intended usage, while a “minimum extent” may be considered the smallest dimension measured according to the intended usage. In some instances, an “extent” may be measured orthogonally within a plane and/or cross-section, but may be, as will be apparent from the particular context, measured differently—such as, but not limited to, angularly, radially, circumferentially (e.g., along an arc), etc.

The terms “monolithic” and “unitary” shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to “an embodiment”, “some embodiments”, “other embodiments”, etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to use the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a “first” element may later be referred to as a “second” element, a “third” element, etc. or may be omitted entirely, and/or a different feature may be referred to as the “first” element. The meaning and/or designation in each instance will be apparent to the skilled practitioner.

The figures illustrate selected components and/or arrangements of medical implants, systems, and methods of manufacturing the same. It should be noted that in any given figure, some features of the medical implants, systems, and methods may not be shown, or may be shown schematically, for simplicity. Additional details regarding some elements may be illustrated in other figures in greater detail. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. As such, it will be understood that the following discussion may apply equally to any and/or all of the components for which there are more than one within the medical implants, systems, and methods of manufacturing, unless explicitly stated to the contrary. The devices and/or methods disclosed herein may provide a number of desirable features and benefits as described in more detail below.

FIG. 1 schematically illustrates selected components and/or arrangements of a medical device system 10. The medical device system 10 may be used to deliver and/or deploy a variety of medical implants (e.g., a cardiovascular medical implant, an occlusive medical implant, a replacement heart valve implant, etc.) to one or more locations within the anatomy, including but not limited to, in some embodiments, the heart. In some embodiments, the medical device system 10 may include a delivery device that can be used for percutaneous delivery of a replacement heart valve implant (e.g., a replacement mitral valve, a replacement aortic valve, etc.) to an area of interest in the anatomy, such as a native heart valve. This, however, is not intended to be limiting as the medical device system 10 and/or the delivery device may also be used for other interventions including valve repair, valvuloplasty, and the like, or other similar interventions.

Figure 2:
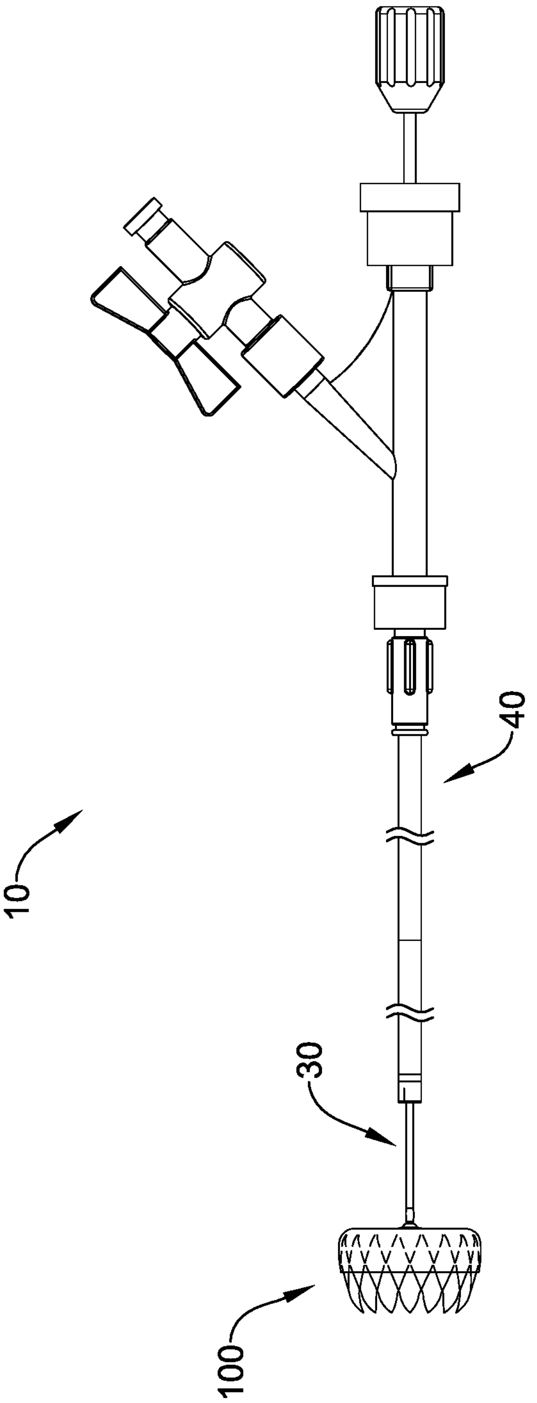

The medical device system 10 including a catheter 40 having a lumen 42 extending from a proximal opening to a distal opening, a core wire 30 slidably disposed within the lumen 42, and a medical implant 100 (e.g., a cardiovascular medical implant, an occlusive medical implant, etc.) having an expandable scaffold configure to shift between a first configuration (e.g., FIG. 1), wherein the medical implant 100 is disposed within the lumen 42 proximate the distal opening in the first configuration, and a second configuration (e.g., FIG. 2), wherein the medical implant 100 and/or the expandable scaffold is configured to shift between the first configuration and the second configuration when the medical implant 100 is disposed distal of the distal opening of the lumen 42 and/or the catheter 40, and/or when the medical implant 100 is unconstrained by the catheter 40. The medical implant 100 may be disposed at and/or releasably connected to a distal portion of the core wire 30. The core wire 30 may be slidably and/or rotatably disposed within the lumen 42 of the catheter 40. In some embodiments, a proximal end of the core wire 30 may extend proximally of a proximal end of the catheter 40 and/or the proximal opening of the lumen 42 for manual manipulation by a clinician or practitioner. In some embodiments, the example medical implant 100 may be removably attached, joined, or otherwise connected to the distal end of the core wire 30. Some suitable, but non-limiting, examples of materials for the medical device system 10, the core wire 30, the catheter 40, and/or the medical implant 100, etc. are discussed below. It is contemplated that any and/or all example occlusive implants disclosed herein may be used in accordance with and/or be associated with the example medical device system 10 described above.

Figure 3:
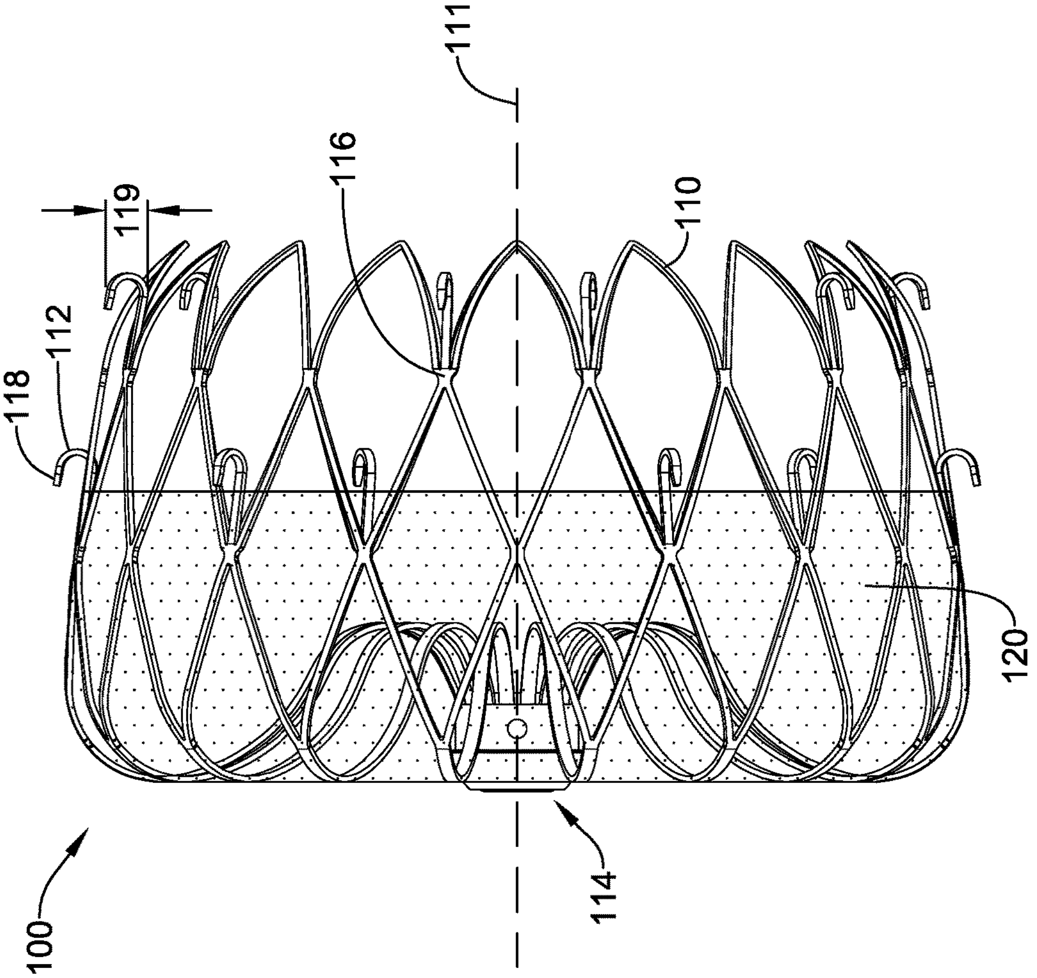
FIG. 3 is a side view of a prior art configuration of a medical implant.

FIG. 3 illustrates selected aspects of the medical implant 100. The medical implant 100 includes an expandable scaffold 110 configured to shift between the first configuration (e.g., FIG. 1) and the second configuration (e.g., FIGS. 2-3). The first configuration may be a radially collapsed configuration and the second configuration may be a radially expanded configuration. The expandable scaffold 110 may have a central longitudinal axis 111. A proximal end 114 of the expandable scaffold 110 may be configured to releasably attach or connect to the distal end of the core wire 30. The proximal end 114 of the expandable scaffold 110 includes a threaded insert configured to engage a threaded member disposed at the distal end of the core wire 30. The expandable scaffold 110 includes a plurality of anchor members 112 each connected to the expandable scaffold 110 at an intersection point 116 between adjacent struts of the expandable scaffold 110. The expandable scaffold 110 includes a plurality of struts, wherein ends of adjacent struts of the plurality of struts are joined together, connected, etc. at the intersection point(s) 116. The free end 118 of the plurality of anchor members 112 extends radially outward from the expandable scaffold 110 in the second configuration. The plurality of anchor members 112 is configured to engage a wall of a left atrial appendage in the second configuration. The medical implant 100 includes an occlusive element 120 coupled to the expandable scaffold 110.

A method of manufacturing the medical implant 100 may include forming and/or cutting the expandable scaffold 110 from a unitary tubular member in the first configuration. Alternatively, the method of manufacturing the medical implant 100 may include forming and/or cutting the expandable scaffold 110 from a flat sheet of material that is later rolled and/or formed into a tubular member. After forming the flat sheet of material into a tubular member, the tubular member may be welded or otherwise fixedly secured into a tubular shape. After cutting the expandable scaffold 110, the method may include forming the expandable scaffold 110 into the second configuration. As part of forming the expandable scaffold 110 into the second configuration, the method may include bending each anchor member of the plurality of anchor members 112. After forming the expandable scaffold 110 into the second configuration, the method may include heat setting the expandable scaffold 110 in the second configuration.

Figure 4:
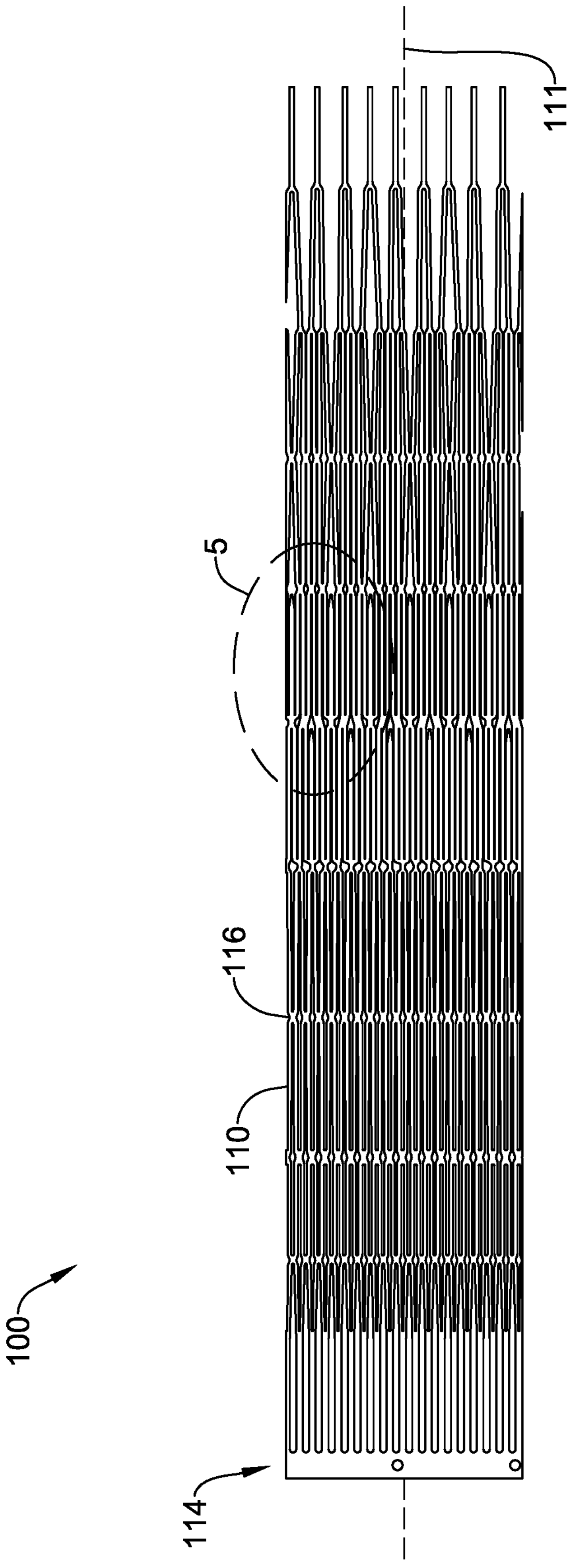
FIG. 4 illustrates a flat pattern of an expandable scaffold of the medical implant of FIG. 3.
Figure 5:
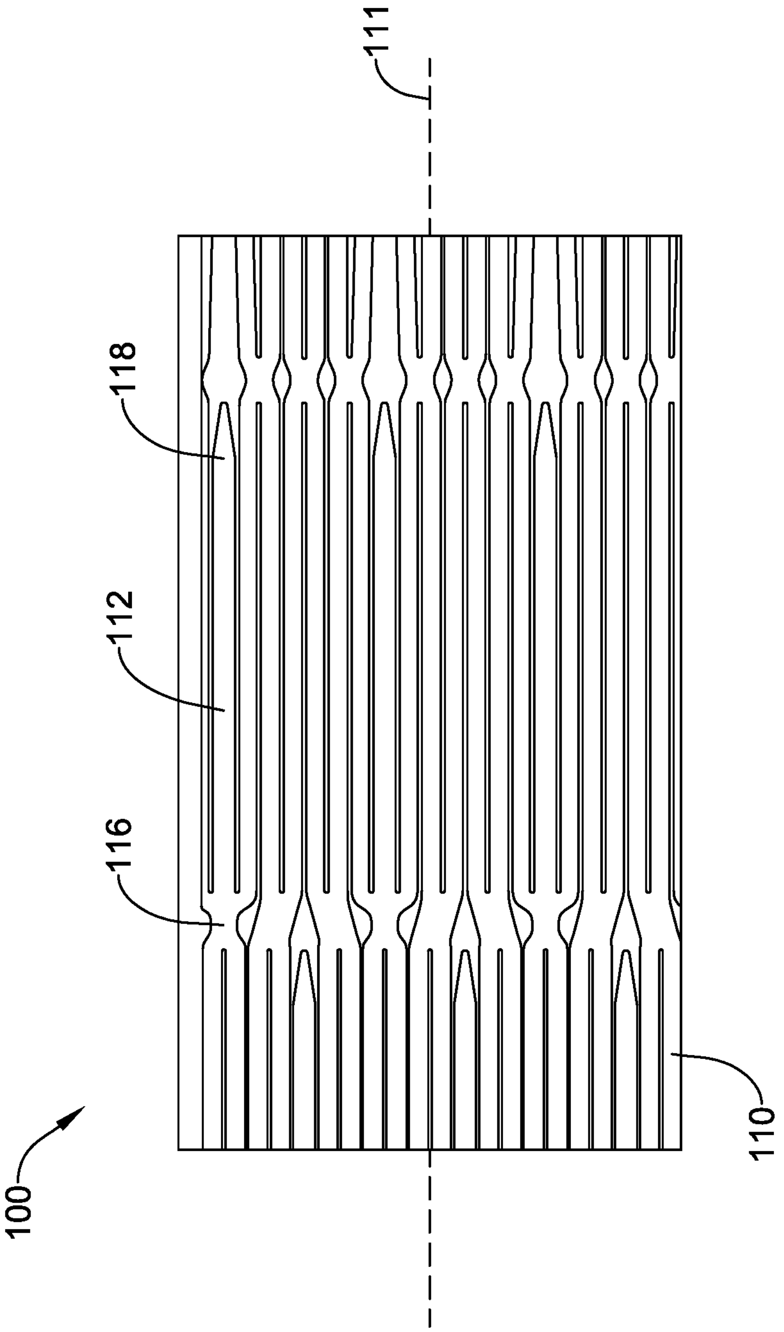
FIG. 5 is a detailed view of a portion of the flat pattern of FIG. 4.

FIG. 4 is a flat pattern view of the expandable scaffold 110 of FIG. 3, and FIG. 5 is a detailed view of a portion of FIG. 4. The flat pattern view is used herein to improve clarity of the disclosure. However, it shall be understood that in some embodiments, forming and/or cutting the expandable scaffold from a unitary tubular member may be preferred and illustration of a flat pattern does not constitute a preference for forming and/or cutting the expandable scaffold from a flat sheet of material.

As illustrated, the expandable scaffold 110 includes the plurality of anchor members 112 connected to the expandable scaffold 110 at the intersection point(s) 116. Each anchor member of the plurality of anchor members 112 includes a free end 118 extending away from the intersection point 116. The plurality of anchor members 112 are oriented substantially parallel to the struts of the expandable scaffold 110 in the first configuration. As part of forming the expandable scaffold 110 into the second configuration, the method includes bending the free end 118 away from the expandable scaffold 110 around a bending axis to the orientation shown in FIG. 3. Each anchor member of the plurality of anchor members 112 extends radially outward from the plurality of struts after bending. The bending axis of each anchor member is oriented transverse or perpendicular to the central longitudinal axis 111 of the expandable scaffold 110 and/or the bending axis is oriented transverse or perpendicular to a longitudinal axis of the struts of the expandable scaffold 110 in the first configuration. The bending axis may be askew from the central longitudinal axis 111 of the expandable scaffold 110 (e.g., the bending axis does not intersect the central longitudinal axis 111). Existing configurations and/or methods may require the plurality of anchor members 112 to each be formed and/or bent individually (e.g., one at a time).

The process of bending the free end(s) 118 of the plurality of anchor members 112 includes and/or introduces significant variability in the height 119 of the anchor members, shown in FIG. 3, as well as the angle of the free end 118 relative to the central longitudinal axis 111 of the expandable scaffold 110 and/or relative to the adjacent struts of the expandable scaffold 110. For proper anchoring after deployment, several manufacturing specifications must be maintained within design tolerances. The manufacturing specifications may include height, angle, radius, skew, etc. The complexity and difficulty associated with the bending process of forming the plurality of anchor members 112, as well as the quantity of anchor members, produce opportunities for the expandable scaffold 110 to be out of specification. For example, the free end 118 may experience spring back after bending. Spring back is a normal byproduct of the bending process and may affect at least the height and/or the angle of the anchor member. Spring back may be at least partially compensated for but can sometimes be unpredictable and/or inconsistent. Disclosed herein are methods and/or configurations that may significantly reduce variation within the expandable scaffold 110, thereby reducing scrap rates, reducing manufacturing costs, and/or improving quality.

Figure 6:
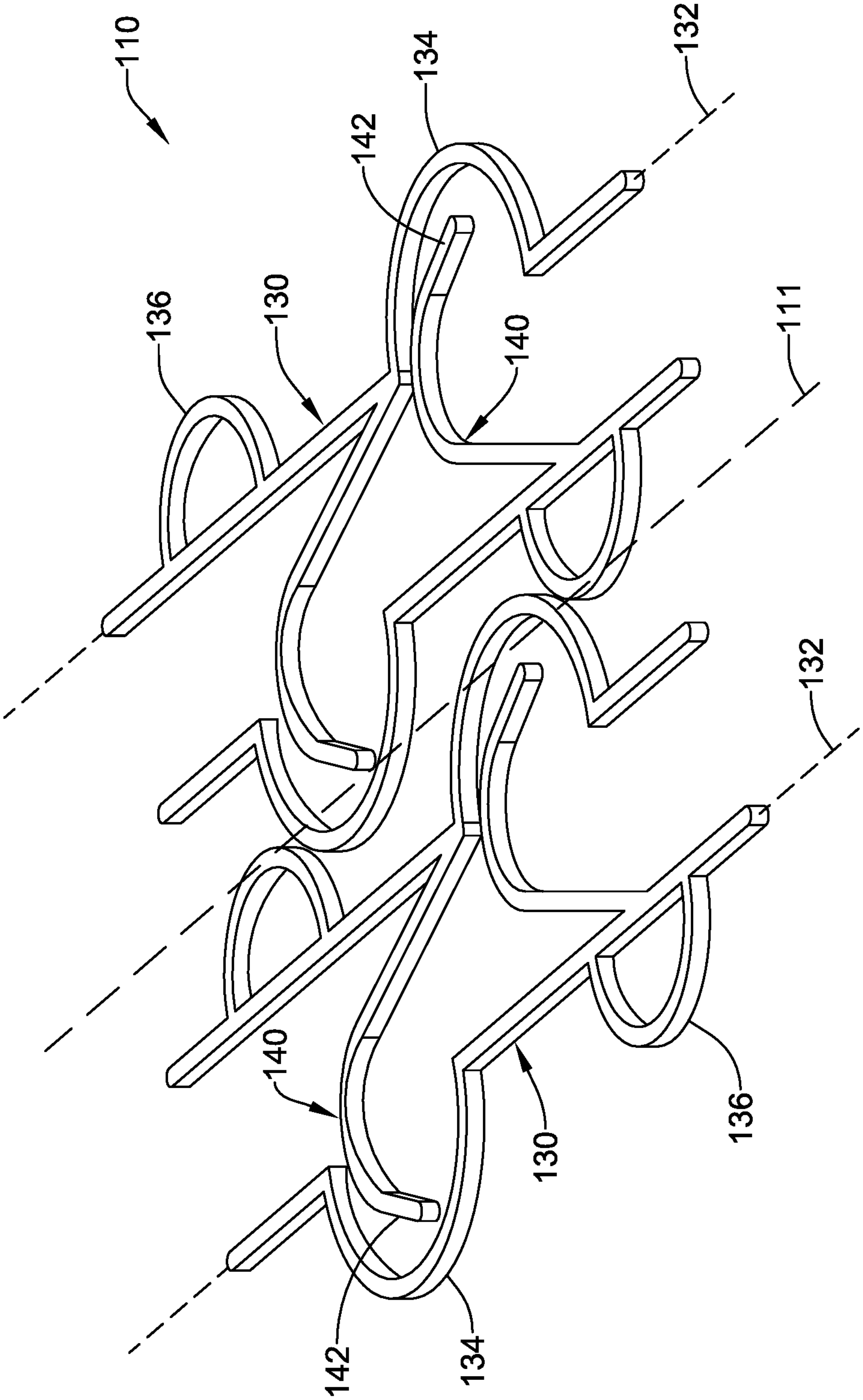
FIG. 6 is a perspective view of a portion of a flat pattern of an expandable scaffold according to the disclosure.

FIG. 6 illustrates a detailed view of a portion of a flat pattern of an alternative configuration for the expandable scaffold 110 that is intended to remedy at least some of the difficulties that arise when bending the plurality of anchor members 112 of FIGS. 3-5. As shown in FIG. 6, the expandable scaffold 110 may include a plurality of struts 130 oriented generally parallel to each other and/or the central longitudinal axis 111 of the expandable scaffold 110 in the first configuration. Each strut of the plurality of struts 130 may include and/or have a longitudinal axis 132 oriented generally parallel to the central longitudinal axis 111 of the expandable scaffold 110 in the first configuration.

The expandable scaffold 110 may include a plurality of anchor members 140 each extending laterally and/or circumferentially from a medial portion of a strut of the plurality of struts 130 of the expandable scaffold 110. Each anchor member of the plurality of anchor members 140 may include a first end fixedly attached to and/or integrally formed with the medial portion of the strut and a free end 142 opposite the first end. In some embodiments, each anchor member may extend in a distal direction from the first end and the free end 142 of each anchor member may be formed into a hook shape having a tip extending in a proximal direction.

In some embodiments, the plurality of struts 130 may be longitudinally discontinuous (e.g., the struts do not extend in a straight line between ends). In some embodiments, at least some struts of the plurality of struts 130 may each include an offset portion 134 and/or a support portion 136 longitudinally offset from and/or longitudinally spaced apart from the offset portion 134. In some embodiments, the offset portion 134 and/or the support portion 136 may be laterally and/or circumferentially offset from the longitudinal axis 132 of the strut. In some embodiments, the offset portion 134 and/or the support portion 136 may extend laterally and/or circumferentially from the strut and/or the longitudinal axis 132 of the strut.

In some embodiments, the free end 142 of each anchor member of the plurality of anchor members 140 may extend laterally and/or circumferentially across the longitudinal axis 132 of an adjacent strut of the plurality of struts 130 in the first configuration. In some embodiments, the offset portion 134 may extend around the free end 142 of the anchor member of an adjacent strut of the plurality of struts 130. In some embodiments, each support portion 136 may be disposed laterally and/or circumferentially opposite the first end of one anchor member of the plurality of anchor members 140 relative to the longitudinal axis 132 of the strut.

A method of manufacturing the medical implant 100 may include cutting the expandable scaffold 110 in the first configuration, as discussed herein, to produce the configuration shown in FIG. 6 for example. In some embodiments, the expandable scaffold 110 may be cut with a laser. In some embodiments, the expandable scaffold 110 may be cut with a waterjet. In some embodiments, the expandable scaffold 110 may be machined. Other manufacturing methods and/or processes are also contemplated.

Figure 7:
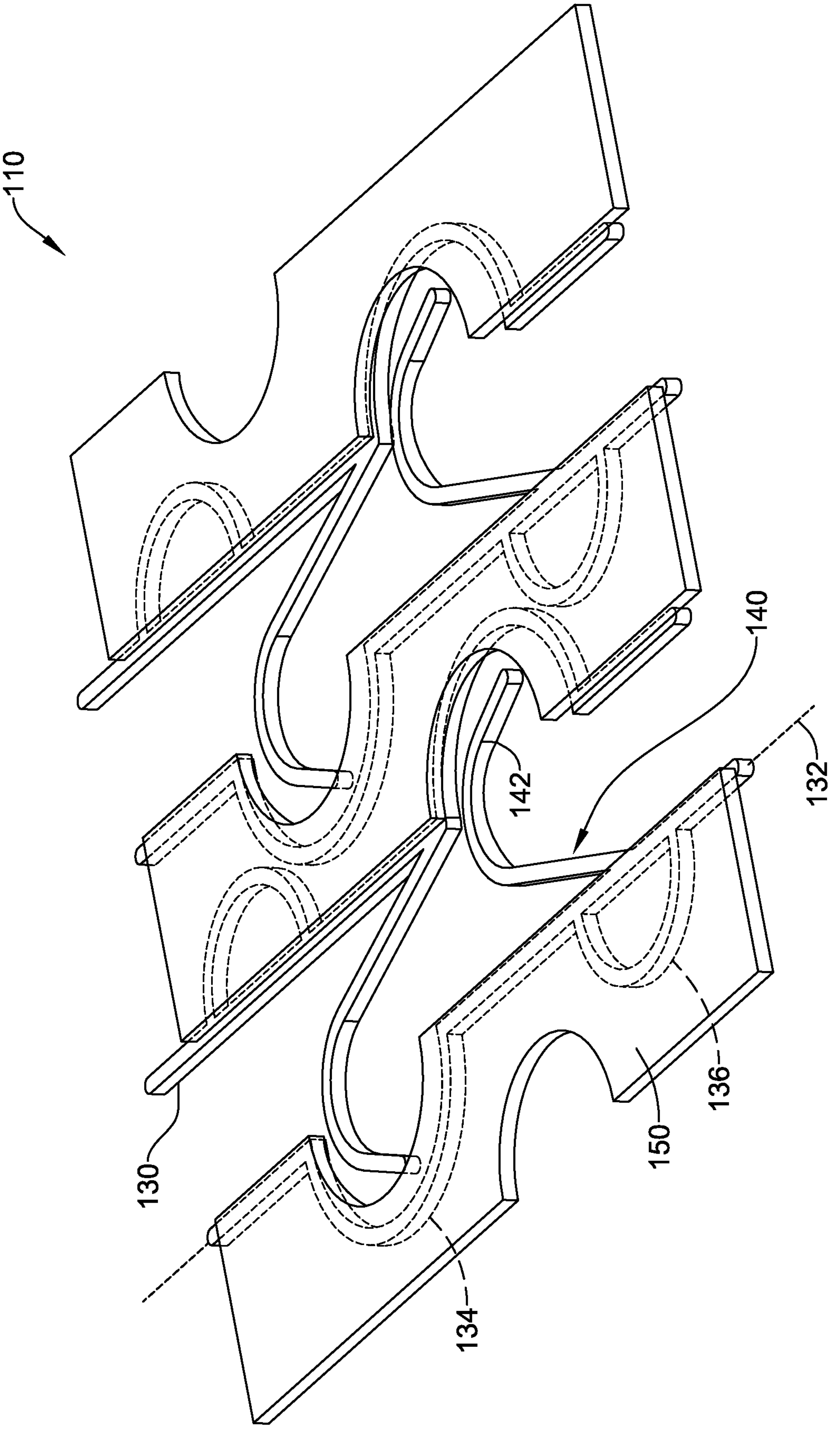
FIGS. 7-8 illustrates selected aspects of a method of manufacturing the expandable scaffold of FIG. 6.
Figure 8:
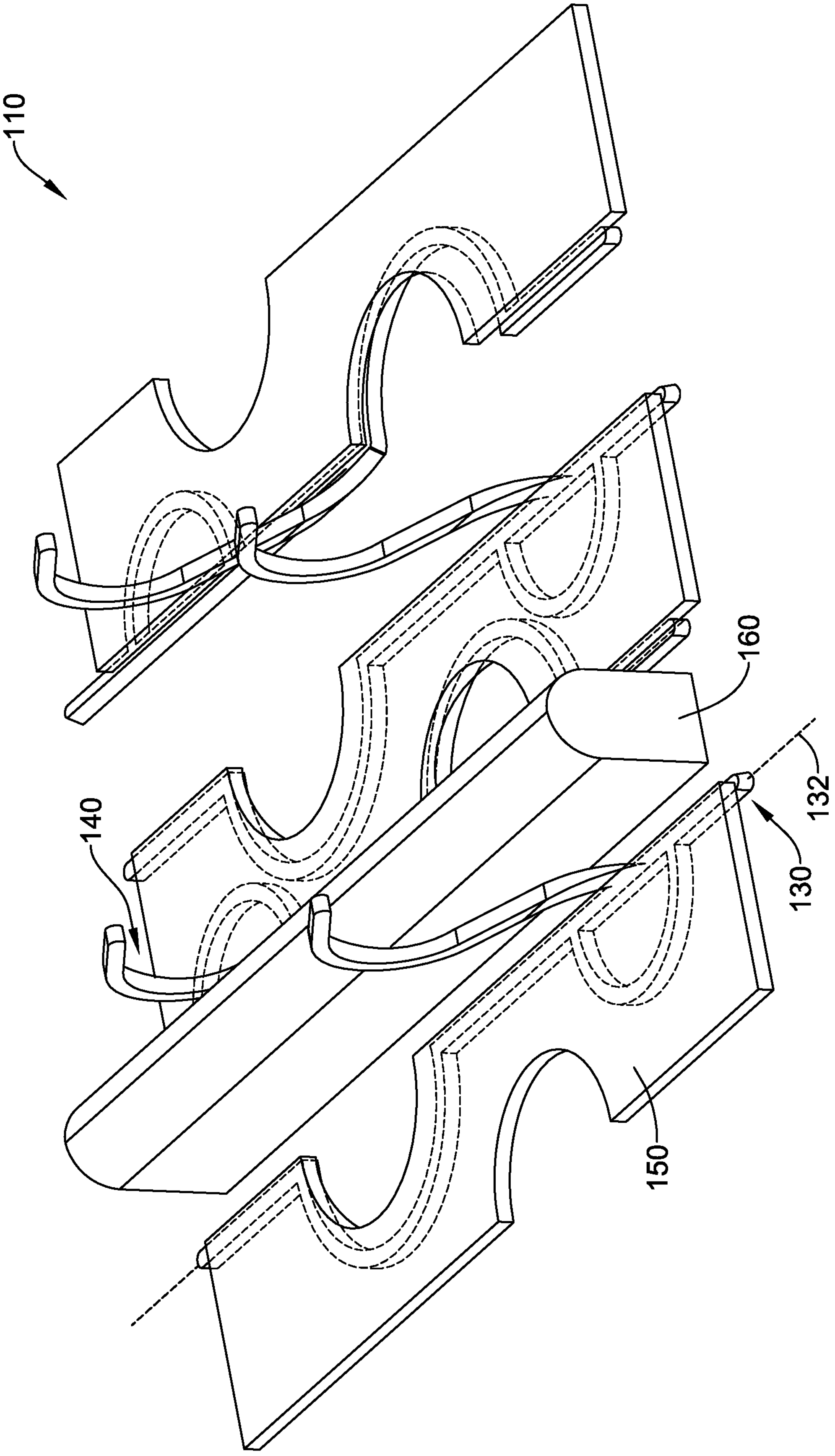

In some embodiments, the method may include forming the expandable scaffold 110 into the second configuration, as at least partially shown in FIGS. 7-8. In some embodiments, forming the expandable scaffold 110 into the second configuration may include restraining the expandable scaffold 110 and/or the plurality of struts 130. In some embodiments, restraining the expandable scaffold 110 and/or the plurality of struts 130 may include grasping and/or pinching at least some of the plurality of struts 130. In some embodiments, restraining the expandable scaffold 110 and/or the plurality of struts 130 may include pressing at least one restraining plate 150 against the expandable scaffold 110 and/or the plurality of struts 130, as shown in FIG. 7. In some embodiments, restraining the expandable scaffold 110 and/or the plurality of struts 130 may include pressing at least one restraining plate 150 against the offset portion 134 and/or the support portion 136. In some embodiments, the expandable scaffold 110, the plurality of struts 130, the offset portion 134, and/or the support portion 136 may be secured against a die, a base plate, or some other suitable structure by the at least one restraining plate 150. The at least one restraining plate 150 may include cutouts 152 that generally align with the offset portion 134 of the plurality of struts 130.

In some embodiments, forming the expandable scaffold 110 into the second configuration may include bending each anchor member along its bending axis. The bending axis may be oriented generally parallel to the longitudinal axis 132 of its respective strut of the plurality of struts 130 in the first configuration. In some embodiments, bending each anchor member along its bending axis may orient at least a portion of the anchor member at about 90 degrees relative to its respective strut in the second configuration. In some embodiments, bending each anchor member along its bending axis may orient the entire anchor member at about 90 degrees relative to its respective strut in the second configuration.

In some embodiments, the expandable scaffold 110 may be formed from a unitary tubular member. In some embodiments, forming the expandable scaffold 110 into the second configuration and/or bending each anchor member may include inserting a punch 160 into an interior of the expandable scaffold 110, which may be understood to be below the expandable scaffold 110 in the views shown in FIGS. 7-8, and moving the punch radially outward relative to the plurality of struts 130, as shown in FIG. 8. The cutouts 152 in the at least one restraining plate 150 may permit the free end 142 of the plurality of anchor members 140 to pass through the at least one restraining plate 150 as the plurality of anchor members 140 is bent. Each anchor member may extend radially outward from the plurality of struts 130 after bending and/or in the second configuration. In some embodiments, moving the punch 160 radially outward relative to the plurality of struts 130 may simultaneously bend more than one of the plurality of anchor members 140. This may reduce the number of bending operations required to form the expandable scaffold 110 into the second configuration, thereby improving manufacturing efficiency and/or cost.

In some embodiments, the expandable scaffold 110 may be formed from a flat sheet of material. In some embodiments, forming the expandable scaffold 110 into the second configuration and/or bending each anchor member may include moving a punch 160 through the expandable scaffold 110 without moving the plurality of struts 130, as shown in FIG. 8. The cutouts 152 in the at least one restraining plate 150 may permit the free end 142 of the plurality of anchor members 140 to pass through the at least one restraining plate 150 as the plurality of anchor members 140 is bent. In some embodiments, moving the punch 160 through the expandable scaffold 110 may simultaneously bend more than one of the plurality of anchor members 140. This may reduce the number of bending operations required to form the expandable scaffold 110 into the second configuration, thereby improving manufacturing efficiency and/or cost. The method may further comprise forming the flat sheet of material into a tubular member such that each anchor member extends radially outward from the plurality of struts 130 in the second configuration.

Figure 9:
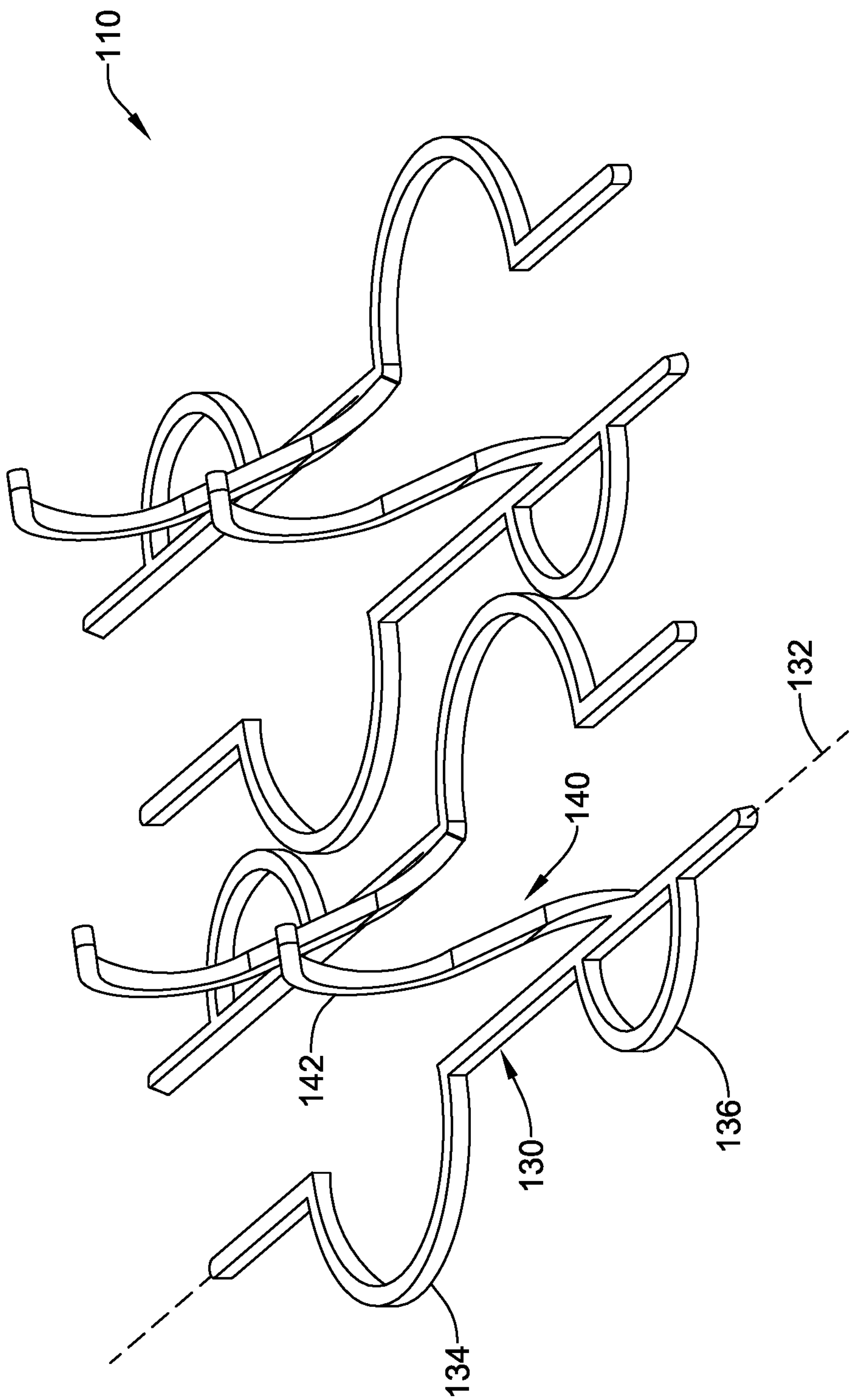
FIG. 9 illustrates selected aspects of the expandable scaffold of FIG. 6 after forming anchor members.

In some embodiments, forming the expandable scaffold 110 into the second configuration and/or bending each anchor member may include preventing the plurality of struts 130 from twisting. As seen in FIG. 9, none of the plurality of struts 130 are twisted after the plurality of anchor members 140 is bent. In some embodiments, bending each anchor member may include preventing its respective strut from rotating about the longitudinal axis 132 of the respective strut as the anchor member is bent. In at least some embodiments, restraining the plurality of struts 130, the offset portion 134, and/or the support portion 136 with the at least one restraining plate 150 may prevent the plurality of struts 130 from twisting and/or rotating about the longitudinal axis 132 as the punch 160 is moved through the expandable scaffold 110 and/or as the punch 160 is moved radially outward relative to the plurality of struts 130, thereby bending each anchor member it contacts along its bending axis. In some embodiments, each anchor member may be bent about and/or along an edge of the at least one restraining plate 150. The bending axis of each anchor member may be oriented generally parallel to the longitudinal axis 132 of each anchor member's respective strut of the plurality of struts 130 in the first configuration. The bending axis may be oriented generally parallel to the central longitudinal axis 111 of the expandable scaffold 110 in the first configuration. In at least some embodiments, the bending axis may be oriented along and/or may be coincident with the edge of the at least one restraining plate 150. In some embodiments, the bending axis may be disposed along and/or immediately adjacent to an edge of each anchor member's respective strut. In some embodiments, the bending axis may be disposed at and/or immediately adjacent to the first end of each anchor member.

Figure 10A:
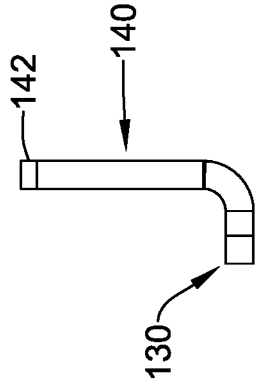
FIGS. 10-10A illustrate selected aspects of an alternative configuration of the expandable scaffold of FIG. 9.
Figure 10:
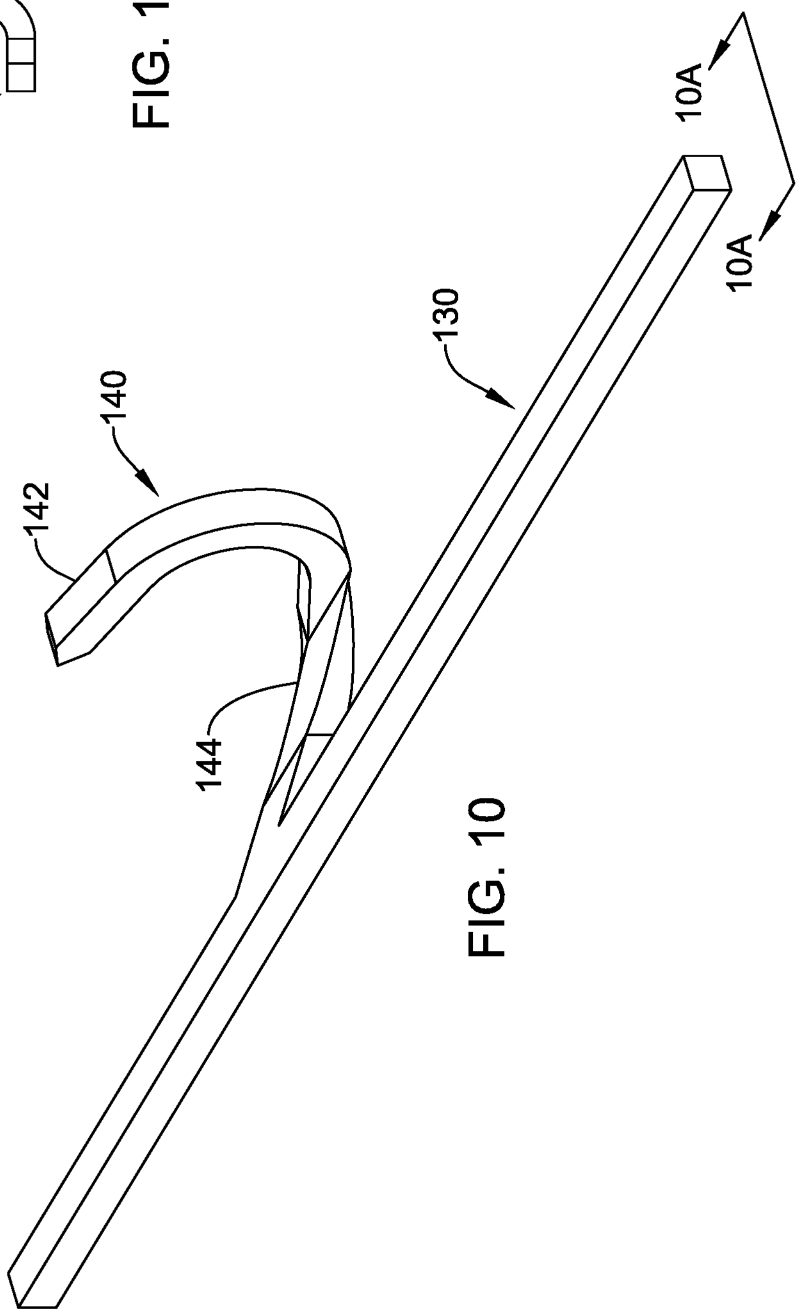

FIG. 10 is a perspective view illustrating an alternative configuration for the plurality of anchor members 140 extending laterally and/or circumferentially from the medial portion of a strut of the plurality of struts 130 of the expandable scaffold 110. FIG. 10A is an end view of the alternative configuration of FIG. 10. Similar to the plurality of anchor members 140 discussed with respect to FIGS. 6-9 above, each anchor member may be bent along its bending axis. In at least some embodiments, the bending axis may be oriented generally parallel to the longitudinal axis 132 of each anchor member's respective strut of the plurality of struts 130. In some embodiments, the bending axis may be spaced apart from each anchor member's respective strut such that the anchor member is bent along a body portion 144 of the anchor member at a location between the first end and the free end 142, thereby orienting at least a portion of the anchor member at about 90 degrees relative to its respective strut in the second configuration.

Figure 11:
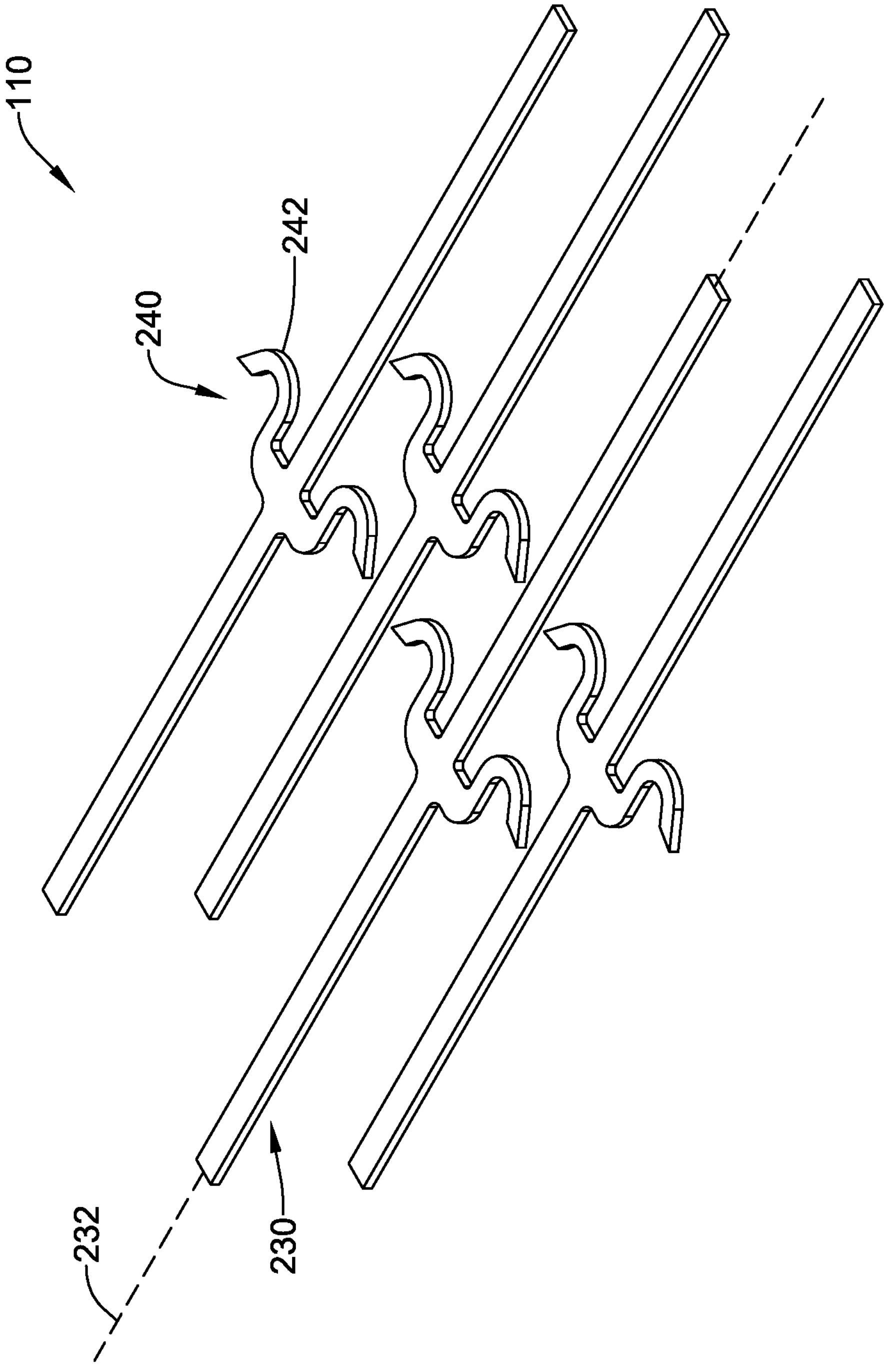
FIG. 11 is a perspective view of a portion of a flat pattern of an expandable scaffold according to the disclosure.

FIGS. 11-15 illustrate selected aspects of a method of manufacturing an alternative configuration for the expandable scaffold 110. FIG. 11 illustrates a detailed view of a portion of a flat pattern of the alternative configuration for the expandable scaffold 110 that is intended to remedy at least some of the difficulties that arise when bending the plurality of anchor members 112 of FIGS. 3-5. As shown in FIG. 11, the expandable scaffold 110 may include a plurality of struts 230 oriented generally parallel to each other and/or the central longitudinal axis 111 of the expandable scaffold 110 in the first configuration. Each strut of the plurality of struts 230 may include and/or have a longitudinal axis 232 oriented generally parallel to the central longitudinal axis 111 of the expandable scaffold 110 in the first configuration.

The expandable scaffold 110 may include a plurality of anchor members 240 each extending laterally and/or circumferentially from a medial portion of a strut of the plurality of struts 230 of the expandable scaffold 110. Each anchor member of the plurality of anchor members 240 may include a first end fixedly attached to and/or integrally formed with the medial portion of the strut and a free end 242 opposite the first end. In some embodiments, each anchor member may extend in a distal direction from the first end and the free end 242 of each anchor member may be formed into a hook shape having a tip extending in a proximal direction. In some embodiments, the plurality of struts 230 may be longitudinally continuous (e.g., the struts extend in a straight line between ends). Anchor members on adjacent struts of the plurality of struts 230 may be longitudinally offset and/or longitudinally spaced apart from each other. In some embodiments, each strut of the plurality of struts 230 may include a pair of anchor members of the plurality of anchor members 240 extending from opposite sides of the strut at a common axial location along the strut. In some embodiments, each strut of the plurality of struts 230 may include multiple pairs of anchor members of the plurality of anchor members 240, wherein each pair extends from opposite sides of the strut at its own common axial location along the strut (e.g., a first pair extends from opposite sides of the strut at a first location, a second pair extends from opposite sides of the strut at a second location, etc.).

A method of manufacturing the medical implant 100 may include cutting the expandable scaffold 110 in the first configuration, as discussed herein, to produce the configuration shown in FIG. 11 for example. In some embodiments, the expandable scaffold 110 may be cut with a laser. In some embodiments, the expandable scaffold 110 may be cut with a waterjet. In some embodiments, the expandable scaffold 110 may be machined. Other manufacturing methods and/or processes are also contemplated.

Figure 13:
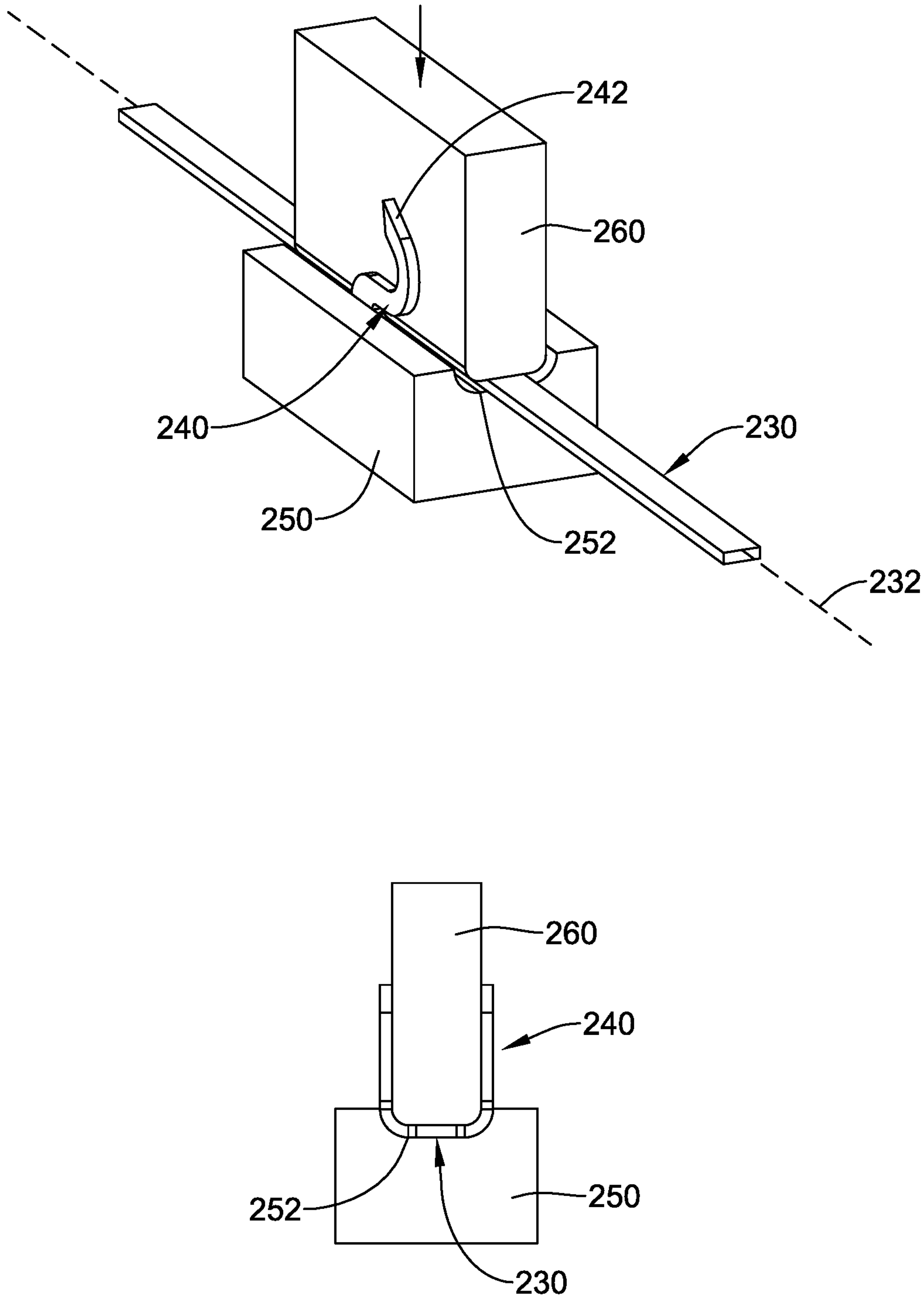
Figure 14:
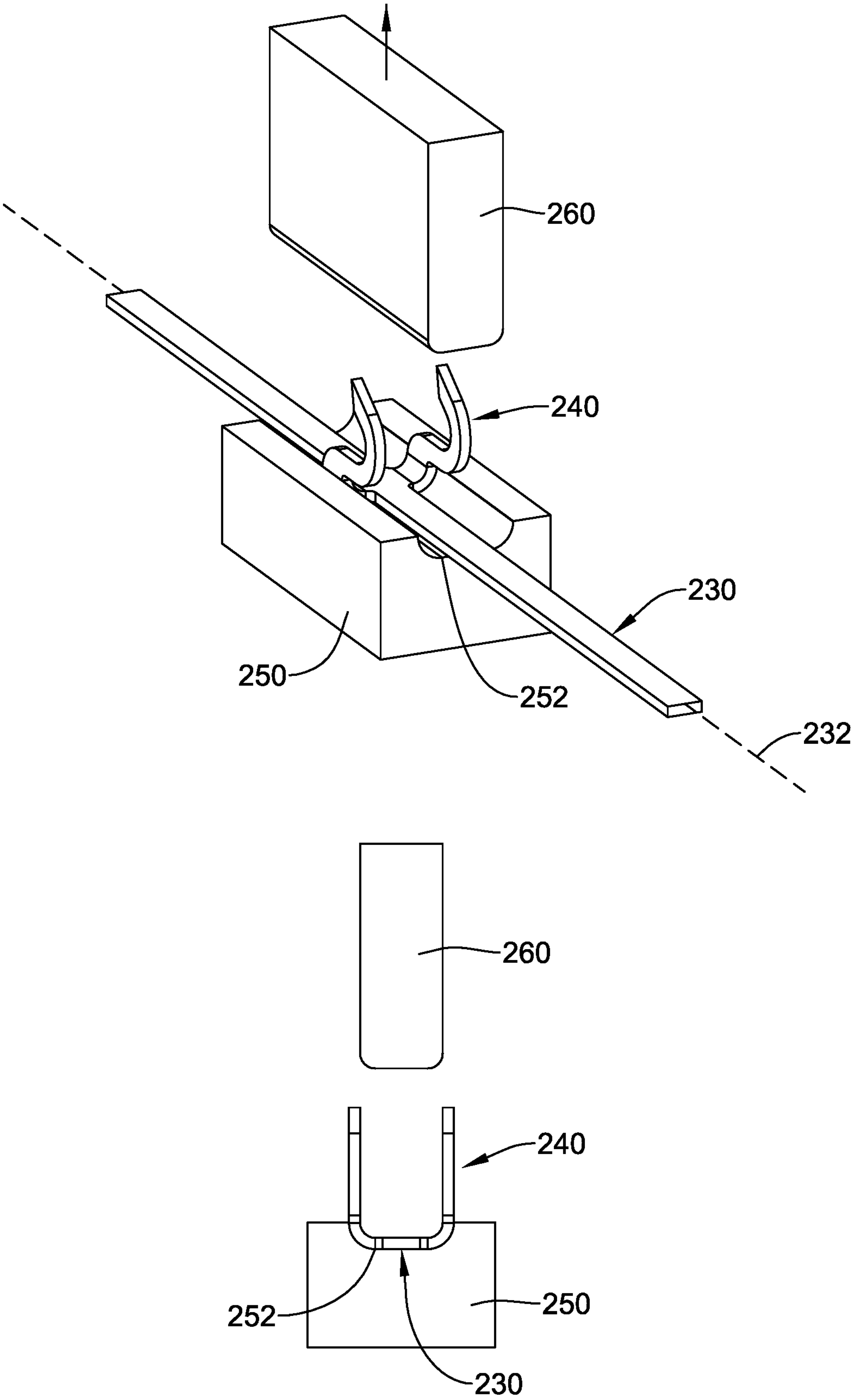
Figure 15:
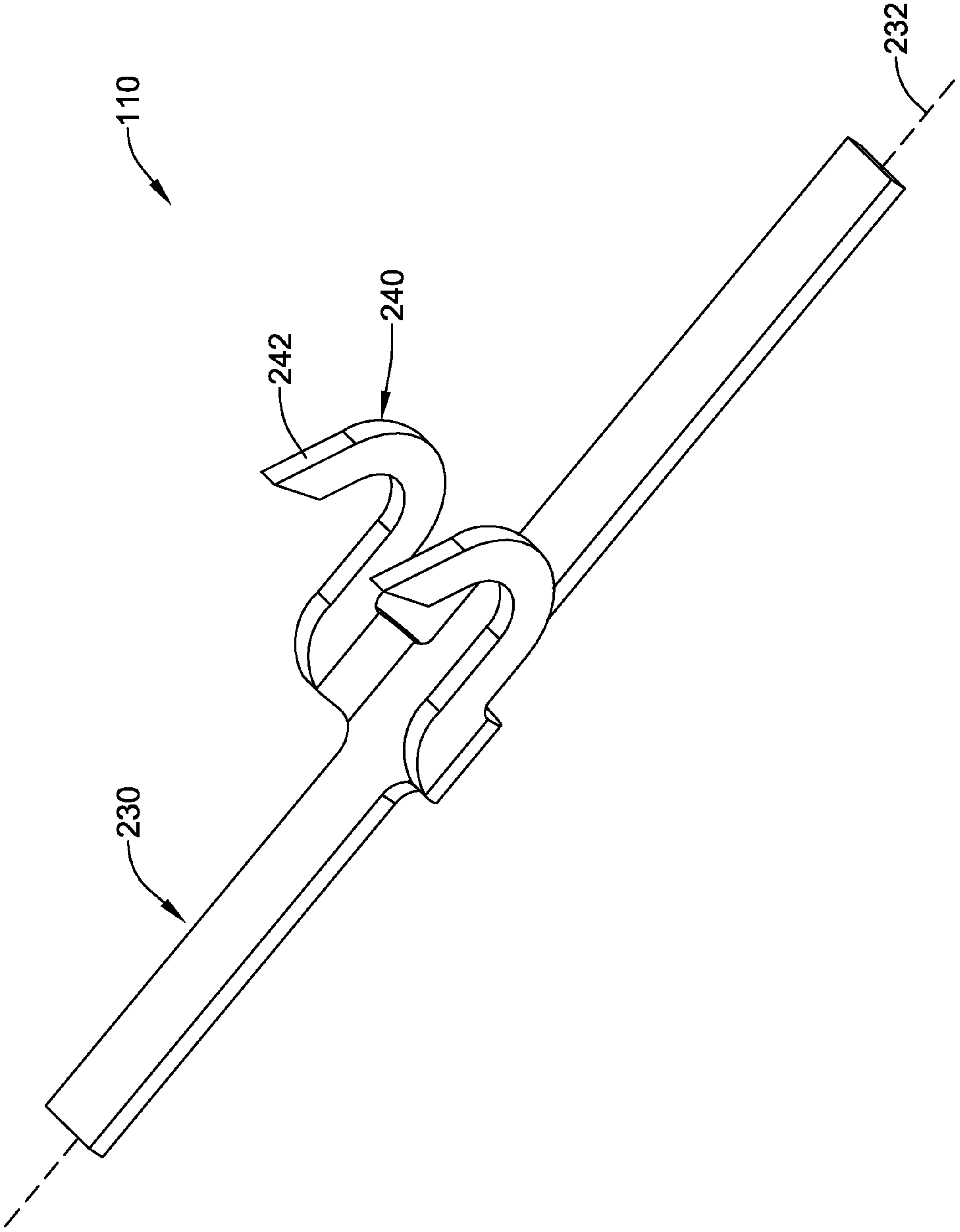
FIG. 15 illustrates selected aspects of the expandable scaffold of FIG. 11 after forming anchor members.

In some embodiments, forming the expandable scaffold 110 into the second configuration may include bending each anchor member along its bending axis. The process of bending each anchor member along its bending axis is illustrated in FIGS. 12-15 using a single strut of the plurality of struts 230, wherein FIG. 15 illustrates the plurality of anchor members 240 after bending and/or in the second configuration. In some embodiments, multiple struts of the plurality of struts 230 may be processed at one time, simultaneously, etc. In some embodiments, each strut of the plurality of struts 230 may be processed one at a time, sequentially, etc. The bending axis may be oriented generally parallel to the longitudinal axis 232 of its respective strut of the plurality of struts 230 in the first configuration. In some embodiments, bending each anchor member along its bending axis may orient at least a portion of the anchor member at about 90 degrees relative to its respective strut in the second configuration. In some embodiments, bending each anchor member along its bending axis may orient the free end 242 of the anchor member at about 90 degrees relative to its respective strut in the second configuration.

Figure 12:
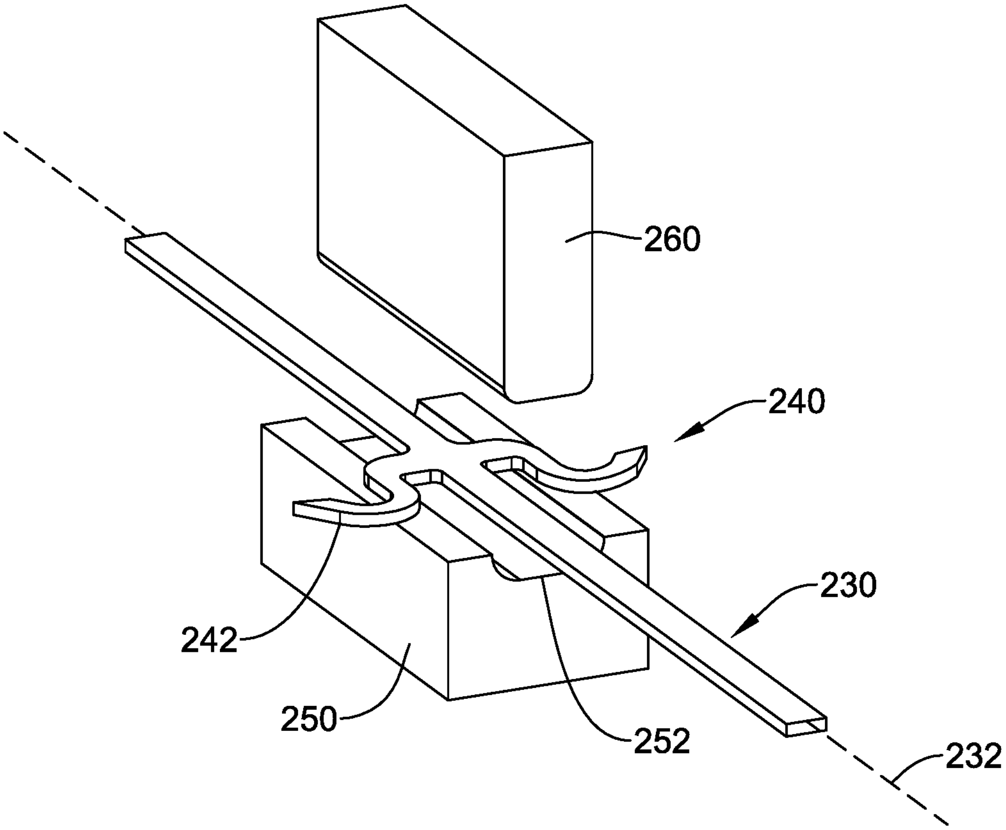
FIGS. 12-14 illustrates selected aspects of a method of manufacturing the expandable scaffold of FIG. 11.
Figure 12:
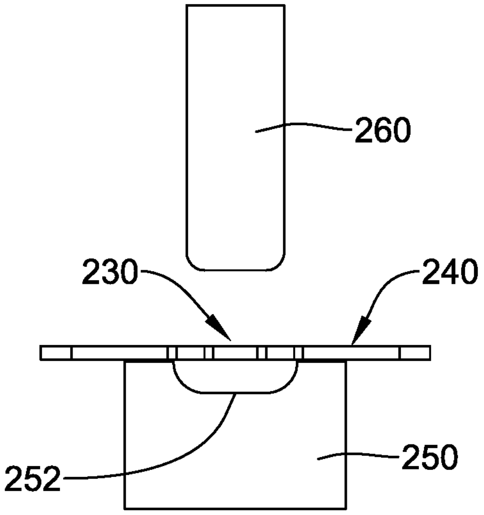

In some embodiments, the expandable scaffold 110 may be formed from a unitary tubular member. In some embodiments, forming the expandable scaffold 110 into the second configuration and/or bending each anchor member may include inserting a die 250 into an interior of the expandable scaffold 110, which may be understood to be below the expandable scaffold 110 in the views shown in FIGS. 12-14. Bending each anchor member may include positioning its respective strut of the plurality of struts 230 over a groove 252 formed in the die 250, as seen in FIG. 12. Bending each anchor member may include urging, pushing, forcing, moving, etc. the respective strut of the plurality of struts 230 into the groove 252 of the die 250 with a punch 260, as seen in FIG. 13. In some embodiments, the punch 260 may be moved radially inward toward the die 250. In some embodiments, the die 250 may be moved radially outward toward the punch 260. The respective strut of the plurality of struts 230 may be squeezed, pinched, clamped, etc. between the punch 260 and the die 250. Each anchor member may extend radially outward from the plurality of struts 230 after bending and/or in the second configuration. In some embodiments, urging, pushing, forcing, moving, etc. the respective strut of the plurality of struts 230 into the groove 252 of the die 250 with the punch 260 may simultaneously bend more than one of the plurality of anchor members 240. This may reduce the number of bending operations required to form the expandable scaffold 110 into the second configuration, thereby improving manufacturing efficiency and/or cost.

In some embodiments, the expandable scaffold 110 may be formed from a flat sheet of material. In some embodiments, forming the expandable scaffold 110 into the second configuration and/or bending each anchor member may include positioning its respective strut of the plurality of struts 230 over the groove 252 formed in the die 250, as seen in FIG. 12. In some embodiments, the longitudinal axis 232 of the respective strut of the plurality of struts 230 may be aligned with and/or parallel to the groove 252 formed in the die 250. Bending each anchor member may include urging, pushing, forcing, moving, etc. the respective strut of the plurality of struts 230 into the groove 252 of the die 250 with the punch 260, as seen in FIG. 13. In some embodiments, the punch 260 may be moved toward the die 250. In some embodiments, the die 250 may be moved toward the punch 260. The respective strut of the plurality of struts 230 may be squeezed, pinched, clamped, etc. between the punch 260 and the die 250. In some embodiments, urging, pushing, forcing, moving, etc. the respective strut of the plurality of struts 230 into the groove 252 of the die 250 with the punch 260 may simultaneously bend more than one of the plurality of anchor members 240. This may reduce the number of bending operations required to form the expandable scaffold 110 into the second configuration, thereby improving manufacturing efficiency and/or cost. The method may further comprise forming the flat sheet of material into a tubular member such that each anchor member extends radially outward from the plurality of struts 230 in the second configuration.

In some embodiments, forming the expandable scaffold 110 into the second configuration and/or bending each anchor member may include preventing the plurality of struts 230 from twisting. As seen in FIGS. 14-15, the plurality of struts 230 is not twisted after the plurality of anchor members 240 is bent. In some embodiments, bending each anchor member may include preventing its respective strut from rotating about the longitudinal axis 232 of the respective strut as the anchor member is bent. In at least some embodiments, squeezing, pinching, clamping, etc. the plurality of struts 230 between the punch 260 and the die 250 may prevent the plurality of struts 230 from twisting and/or rotating about the longitudinal axis 232 as the punch 260 is moved toward the die 250, thereby bending each anchor member it contacts along its bending axis. In some embodiments, each anchor member may be bent about and/or along an edge of the punch 260. The bending axis of each anchor member may be oriented generally parallel to the longitudinal axis 232 of each anchor member's respective strut of the plurality of struts 230 in the first configuration. The bending axis may be oriented generally parallel to the central longitudinal axis 111 of the expandable scaffold 110 in the first configuration. In at least some embodiments, the bending axis may be oriented along and/or may be coincident with the edge of the punch 260. In some embodiments, the bending axis may be disposed along and/or adjacent to an edge of each anchor member's respective strut. In some embodiments, the bending axis may be disposed at and/or immediately adjacent to the first end of each anchor member.

In some embodiments, the method of manufacturing the medical implant 100 may include heat setting the expandable scaffold 110 and/or the plurality of anchor members 240 in the second configuration. In some embodiments, the method of manufacturing the medical implant 100 may include heat setting the expandable scaffold 110 and/or the plurality of anchor members 240 in the second configuration after bending the plurality of anchor members 240 radially outward from the plurality of struts 230. In some embodiments, the method of manufacturing the medical implant 100 may include heat setting at least some of the plurality of anchor members 240 after bending some of the plurality of anchor members 240 radially outward from the plurality of struts 230 and before all of the plurality of anchor members 240 have been bent radially outward from the plurality of struts 230. In some embodiments, the method of manufacturing the medical implant 100 may include heat setting the expandable scaffold 110 and/or the plurality of anchor members 240 in the second configuration after bending all of the plurality of anchor members 240 radially outward from the plurality of struts 230. Other configurations and/or orders of operations are also contemplated.

In some embodiments, the method of manufacturing the medical implant 100 may include securing the occlusive element 120 to the expandable scaffold 110. In some embodiments, at least some of the plurality of anchor members 240 may extend through the occlusive element 120 in the second configuration. In some embodiments, the occlusive element 120 may be disposed along an exterior surface of the expandable scaffold 110. In some embodiments, the occlusive element 120 may cover at least 20% of the expandable scaffold 110 in the second configuration. In some embodiments, the occlusive element 120 may cover at least 30% of the expandable scaffold 110 in the second configuration. In some embodiments, the occlusive element 120 may cover at least 40% of the expandable scaffold 110 in the second configuration. In some embodiments, the occlusive element 120 may cover at least 50% of the expandable scaffold 110 in the second configuration. In some embodiments, the occlusive element 120 may cover at least 60% of the expandable scaffold 110 in the second configuration. In some embodiments, the occlusive element 120 may cover at least 70% of the expandable scaffold 110 in the second configuration. Other configurations are also contemplated.

The methods of manufacturing described herein may produce the expandable scaffold 110 with significantly less variability. For example, whereas bending anchor members to form each hook shape individually (e.g., FIG. 3) may have a height tolerance of +/−0.005 inches, forming the hook shape via the cutting step may have a height tolerance of +/−0.001 inches or less. In this example, variability may be reduced by about 5 times, about 8 times, 10 times, etc. In another example, whereas bending anchor members to form each hook shape individually (e.g., FIG. 3) may have an angle tolerance of +/−10 degrees, forming the hook shape via the cutting step may have an angle tolerance of +/−1 degree or less. In this example, variability may be reduced by about 8 times, about 10 times, about 12 times, about 14 times, etc. As a result, incidence of manufacturing scrap may be significantly reduced, thereby improving throughput and reducing the cost of goods. These are only examples, and additional and/or other benefits are also contemplated and/or expected.

The materials that can be used for the various components of the medical implants, systems, and methods of manufacturing disclosed herein may include those commonly associated with medical devices. For simplicity purposes, the following discussion refers to the system. However, this is not intended to limit the system, devices, and/or methods described herein, as the discussion may be applied to other elements, members, components, or devices disclosed herein, such as, but not limited to, the expandable scaffold, the plurality of struts, the plurality of anchor members, the occlusive element, etc. and/or elements or components thereof.

In some embodiments, the system and/or components thereof may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN®), polyether block ester, polyurethane (for example, Polyurethane 85A), polypropylene (PP), polyvinylchloride (PVC), polyether-ester (for example, ARNITEL®), ether or ester based copolymers (for example, butylene/poly(alkylene ether) phthalate and/or other polyester elastomers such as HYTREL®), polyamide (for example, DURETHAN® or CRISTAMID®), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID®), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, Elast-Eon® or ChronoSil®), biocompatible polymers, other suitable materials, or mixtures, combinations, copolymers thereof, polymer/metal composites, and the like. In some embodiments, the system and/or components thereof can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof, or any other suitable material.

In some embodiments, portions or all of the system and/or components thereof may be doped with, made of, or otherwise include a radiopaque material. Radiopaque materials are understood to be materials capable of producing a relatively bright image on a fluoroscopy screen or another imaging technique (e.g., ultrasound, etc.) during a medical procedure. This relatively bright image aids a user in determining the location of the system. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the system to achieve the same result.

In some embodiments, a degree of Magnetic Resonance Imaging (MRI) compatibility is imparted into the system. For example, the system and/or components or portions thereof may be made of a material that does not substantially distort the image and create substantial artifacts (e.g., gaps in the image). Certain ferromagnetic materials, for example, may not be suitable because they may create artifacts in an MRI image. The system or portions thereof may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the system may include a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. In some embodiments, the yarns may be made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun types. The type and denier of the yarn chosen may be selected in a manner which is forms a biocompatible system.

In some embodiments, the system and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethyl ketone)); anti-protein and/or anti-bacterial agents (such as 2-methacryroyloxyethyl phosphorylcholine (MPC) and its polymers or copolymers); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed:

1. A method of manufacturing a medical implant for occluding a left atrial appendage, comprising:

cutting an expandable scaffold in a first configuration;

wherein the expandable scaffold includes a plurality of struts having ends joined together at intersection points and a plurality of anchor members extending from the plurality of struts such that each anchor member extends from a medial portion of a strut of the plurality of struts;

forming the expandable scaffold into a second configuration;

wherein forming the expandable scaffold into the second configuration includes bending each anchor member along a bending axis of each anchor member, the bending axis being oriented parallel to a longitudinal axis of a respective strut of the plurality of struts, wherein forming the expandable scaffold into the second configuration further includes preventing the plurality of struts from twisting; and heat setting the expandable scaffold in the second configuration.

2. The method of claim 1, wherein the expandable scaffold is cut with a laser.

3. The method of claim 1, wherein the first configuration is a radially collapsed configuration and the second configuration is a radially expanded configuration.

4. The method of claim 1, wherein each anchor member extends radially outward from the plurality of struts after bending.

5. The method of claim 1, wherein bending each anchor member further includes preventing the respective strut from rotating about the longitudinal axis of the respective strut as the anchor member is bent.

6. The method of claim 1, wherein the expandable scaffold is formed from a unitary tubular member.

7. The method of claim 6, wherein bending each anchor member includes:

inserting a die into an interior of the expandable scaffold;

positioning the respective strut over a groove formed in the die; and urging the respective strut into the groove with a punch.

8. The method of claim 1, wherein the expandable scaffold is formed from a flat sheet of material.

9. The method of claim 8, wherein bending each anchor member includes:

positioning the respective strut over a groove formed in a die; and urging the respective strut into the groove with a punch.

10. The method of claim 8, further comprising forming the flat sheet of material into a tubular member.

11. A method of manufacturing a medical implant for occluding a left atrial appendage, comprising:

cutting an expandable scaffold in a first configuration;

wherein the expandable scaffold including a plurality of struts having ends joined together at intersection points and a plurality of anchor members extending from the plurality of struts such that each anchor member extends from a medial portion of a strut of the plurality of struts;

forming the expandable scaffold into a second configuration;

wherein forming the expandable scaffold into the second configuration includes bending each anchor member along a bending axis of each anchor member, the bending axis being oriented parallel to a longitudinal axis of a respective strut of the plurality of struts, wherein forming the expandable scaffold into the second configuration further includes preventing the plurality of struts from twisting;

heat setting the expandable scaffold in the second configuration; and securing an occlusive element to the expandable scaffold.

12. The method of claim 11, wherein at least some of the plurality of anchor members extend through the occlusive element in the second configuration.

13. The method of claim 11, wherein the occlusive element is disposed along an exterior surface of the expandable scaffold.

14. The method of claim 13, wherein the occlusive element covers at least 30% of the expandable scaffold in the second configuration.

* * * * *